US008968349B2

(12) United States Patent
Sakakibara

(10) Patent No.: US 8,968,349 B2
(45) Date of Patent: Mar. 3, 2015

(54) ACUPRESSURE APPLIANCE

(71) Applicant: Masao Sakakibara, Handa (JP)

(72) Inventor: Masao Sakakibara, Handa (JP)

( * ) Notice: Subject to any disclaimer, the term of this patent is extended or adjusted under 35 U.S.C. 154(b) by 28 days.

(21) Appl. No.: 13/791,747

(22) Filed: Mar. 8, 2013

(65) Prior Publication Data

US 2013/0204293 A1    Aug. 8, 2013

Related U.S. Application Data

(63) Continuation of application No. PCT/JP2011/070769, filed on Sep. 12, 2011.

(30) Foreign Application Priority Data

Sep. 13, 2010   (JP) .................................. 2010-204877
Sep. 12, 2011   (WO) .................. PCT/JP2011/070769

(51) Int. Cl.
*A61M 29/00*   (2006.01)
*A61B 17/00*   (2006.01)
*A61H 39/04*   (2006.01)

(52) U.S. Cl.
CPC ................ *A61B 17/00* (2013.01); *A61H 39/04* (2013.01); *A61H 2201/1284* (2013.01); *A61H 2201/1604* (2013.01); *A61H 2201/1609* (2013.01); *A61H 2201/1614* (2013.01); *A61H 2201/1623* (2013.01); *A61H 2201/168* (2013.01); *A61H 2201/1695* (2013.01); *A61H 2203/0456* (2013.01); *A61H 2205/04* (2013.01); *A61H 2205/062* (2013.01); *A61H 2205/081* (2013.01)
USPC ........................................................ 606/194

(58) Field of Classification Search
CPC ........................... A61B 17/1325; A61H 39/04
USPC ........ 606/204, 189; 601/134–137, 11, 23, 24, 601/27; 482/10, 139, 11; 297/391; 135/120.3, 120.4, 124; 5/637, 652, 5/646, 648, 640; 248/118, 118.5; 403/397, 400
See application file for complete search history.

(56) References Cited

U.S. PATENT DOCUMENTS 2,856,941 A * 10/1958 O'Neal ........................ 135/137
5,070,807 A * 12/1991 Lewis ........................... 114/361
(Continued)

FOREIGN PATENT DOCUMENTS

JP       53-30790 A     8/1976
JP       53-114409      2/1977
(Continued)

OTHER PUBLICATIONS

Office Action dated Mar. 4, 2014, in counterpart Canadian Patent Application No. 2811079, 2 pages.
(Continued)

*Primary Examiner* — Todd Manahan
*Assistant Examiner* — Erich Herbermann
(74) *Attorney, Agent, or Firm* — Tracy M. Heims; Apex Juris, pllc

(57) ABSTRACT

An acupressure appliance to apply pressure to body parts. The acupressure appliance includes a pair of curved rod-like pressure units and a connector connecting the pair of curved rod-like pressure units in a lateral direction. Each pressure unit includes a convex-curved segment of a chevron shape curved continuously in an axial direction, and the pair of curved rod-like pressure units are spaced apart from each other in the lateral direction.

16 Claims, 22 Drawing Sheets

(56) References Cited

U.S. PATENT DOCUMENTS 6,276,382 B1 * 8/2001 Bindschatel et al. ............ 135/96
6,289,909 B1 * 9/2001 Wood ............................ 135/124

FOREIGN PATENT DOCUMENTS

| | | |
|---|---|---|
| JP | 5-44130 | 6/1993 |
| JP | 11-244113 A | 9/1999 |
| JP | 3063299 | 10/1999 |
| JP | 2005-224369 A | 8/2005 |
| JP | 2006-288986 | 10/2006 |

OTHER PUBLICATIONS

Toru Namikoshi, "Kenko no izumi shiatsu kyoshitsu", 1979, pp. 22, 23, 48, 72 (with its English translation).

* cited by examiner

FIG. 13A
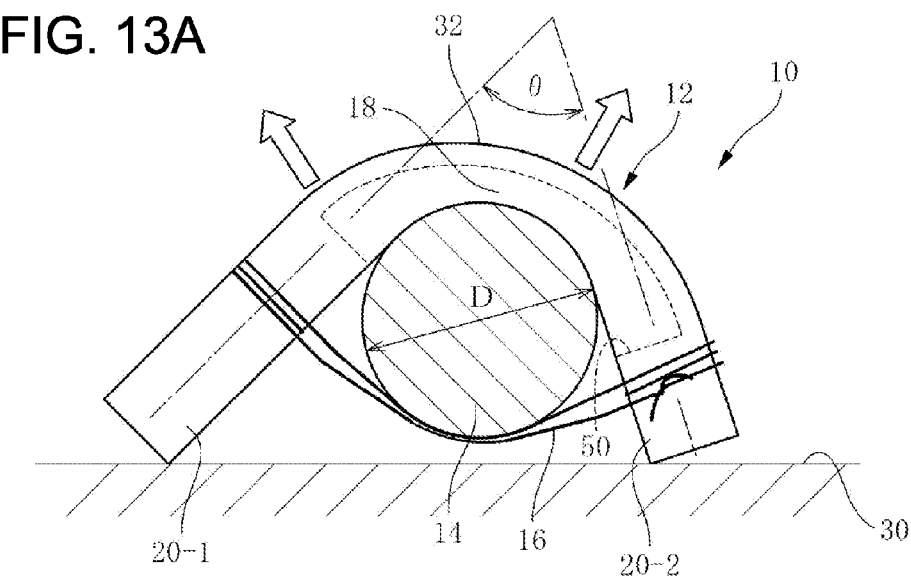
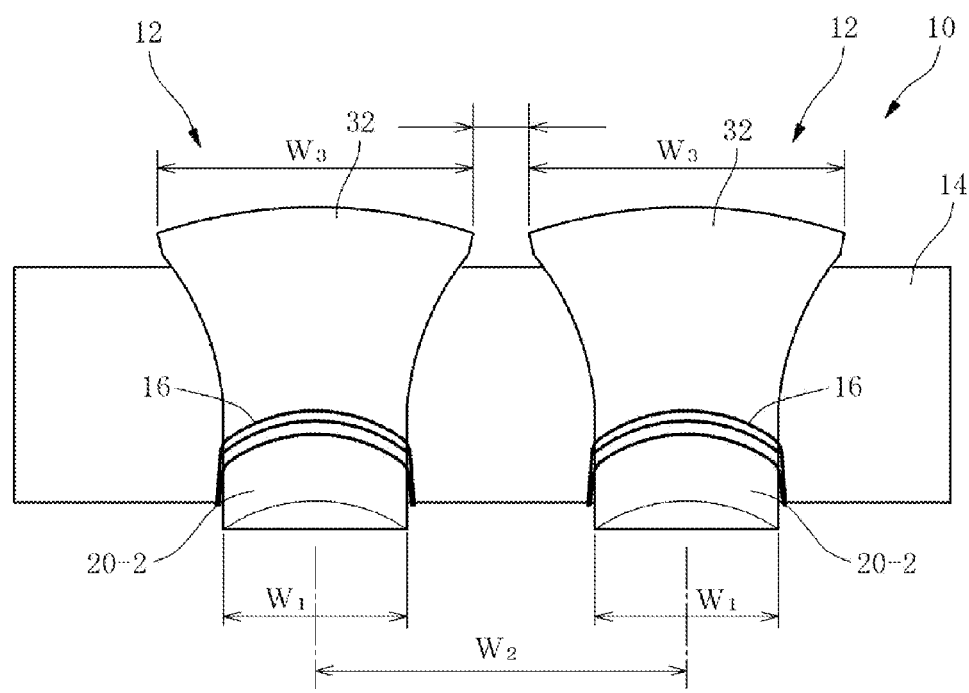
FIG. 13B

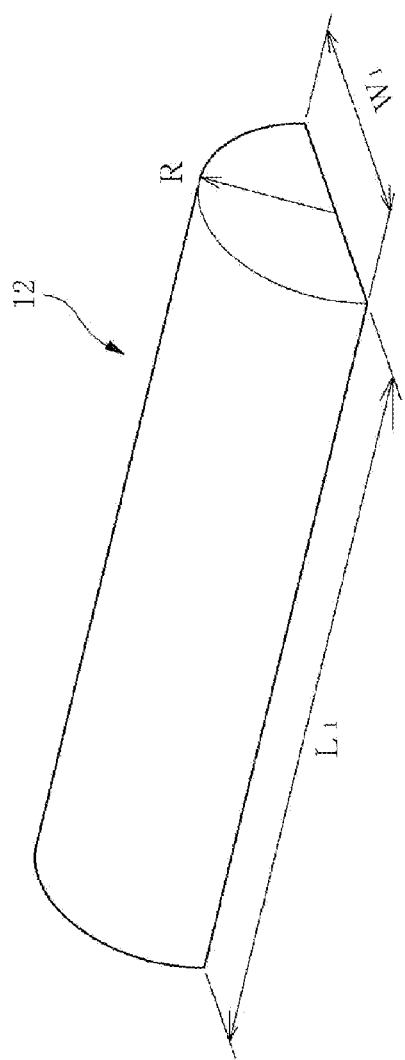
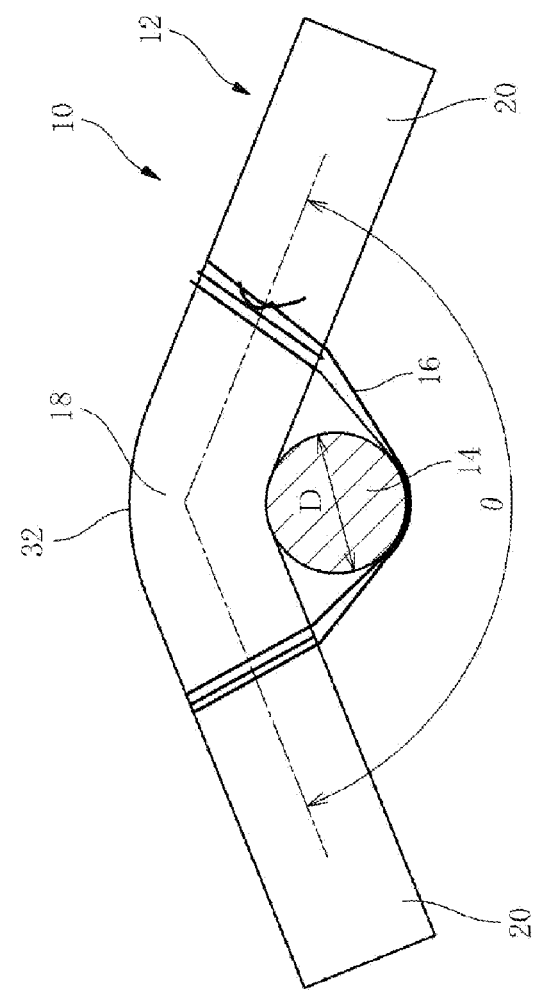
FIG. 15A
FIG. 15B

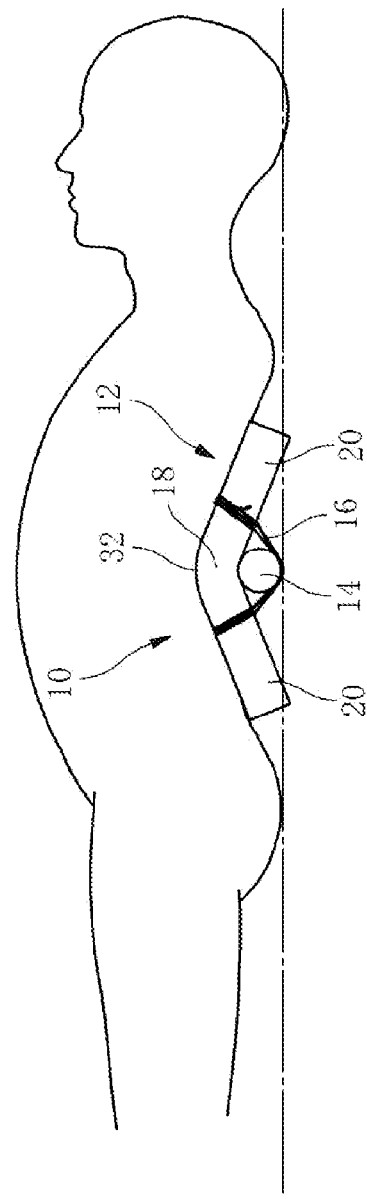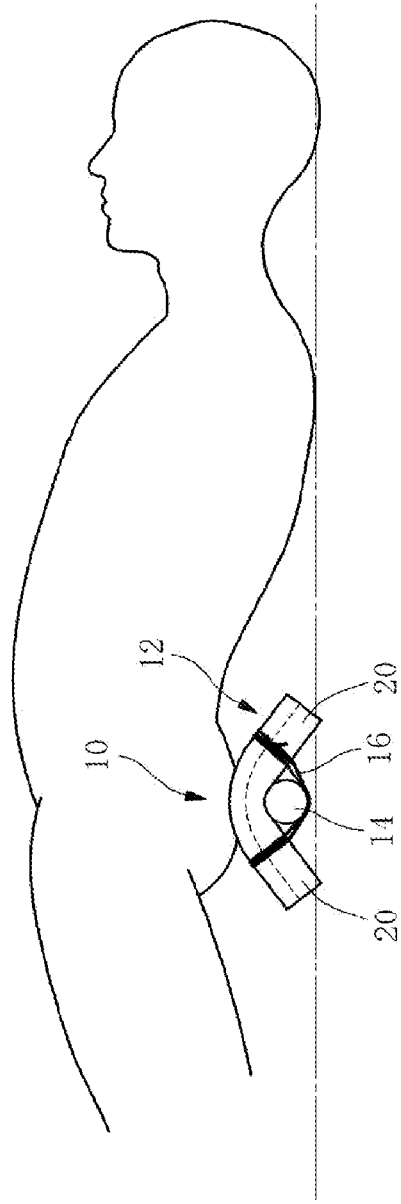
FIG. 17A
FIG. 17B

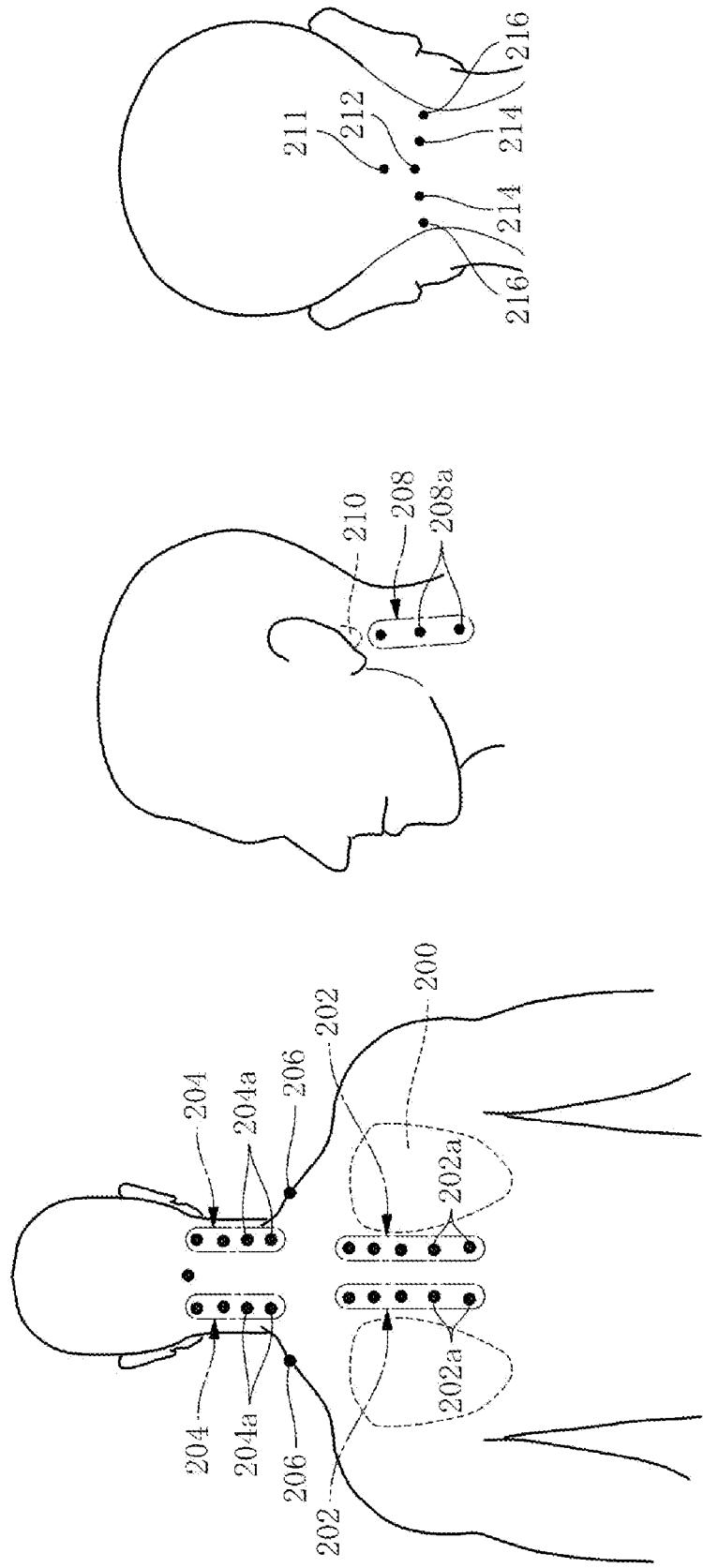

Prior Art

Prior Art

Prior Art

Prior Art

ACUPRESSURE APPLIANCE

CROSS REFERENCE TO RELATED APPLICATIONS

This is a continuation application of International Patent Application No. PCT/JP2011/070769 filed on Sep. 12, 2011 claiming priority upon Japanese Patent Application No. 2010-204877 filed on Sep. 13, 2010, of which full contents are incorporated herein by reference.

BACKGROUND OF THE INVENTION

1. Field of the Invention

The present invention relates to an acupressure appliance and more particularly to an acupressure appliance suitable for use in mainly removal or alleviation of the symptom of stiff shoulders.

2. Description of the Background Art

Stiff shoulders are considered to bear so-called "stiffness" which is caused by muscle fatigue. Muscle fatigue is triggered by stiffened muscles due to persistent tension of muscles in the trapezius to support the head and arm (i.e. muscles found in the area from both sides of the spine to the back of the neck (rear neck part)) and its periphery, which causes circulation failure and poor blood flow, resulting in accumulation of fatigue substances as oxygen and nutrients fail to be delivered to terminal areas. It is usually not limited to stiff shoulders but involves stiff neck.

As a remedy, an acupressure therapy has been widely practiced by chiropractors as an effective therapy.

The acupressure therapy here refers to a therapy in which a chiropractor places his fingers (i.e. finger pads) on a particular area of the patient's body and leans his weight thereon to press it. In this acupressure therapy, it is thought to be effective to apply acupressure along the interscapular regions between the scapulae and the spine and the upper scapular regions above the scapulae in the upper shoulders and further along neck muscles.

FIG. 18A shows the interscapular regions and the rear neck parts (i.e. rear part of neck muscles) along with effective pressure points (or acupressure points) as acupressure regions disclosed in Non-Patent Document (see pages 23 and 72). FIG. 18A further shows the upper scapular regions serving as pressure points (or acupressure points).

In FIG. 18A, 200 is the scapula, 202 is the interscapular region between the scapula 200 and the spine, 202a is a pressure point in the interscapular region 202.

Also in FIG. 18A, 204 is the rear neck part and 204a is a pressure point in the rear neck part 204.

Furthermore, 206 is the upper scapular region positioned above the scapula in the upper shoulder and serves as a pressure point.

FIG. 18B shows the side neck part as an acupressure region along with effective pressure points as disclosed in Non-Patent Document (see pages 48 and 22).

In FIG. 18B, 208 is the side neck part and 208a is a pressure point in the side neck part.

Note that 210 is the mastoid.

In addition to the above, there are many "acupressure points" known as effective pressure points in the vicinity of the first cervical vertebra (atlas vertebra) which is positioned uppermost in the cervical vertebra, or more precisely, in neck muscles to support the skull in the area above the pair of right and left mastoids from one side to the other side thereof.

FIG. 18C shows such acupressure points as disclosed in the following Patent Document 1.

In FIG. 18C, 211 is "fuufu" (or fengfu in the international standard acupuncture terms), 212 is "amon" (or yamen therein), 214 is "tenchuu" (or tianzhu therein) and 216 is "fuuchi" (or fengchi therien).

It is, however, often difficult to receive acupressure treatment by chiropractors all the time or immediately when having the symptom of stiff shoulders.

Thus, various kinds of acupressure appliances have been proposed to allow users to apply acupressure treatment by themselves.

For example, the following Patent Document 1 discloses an acupressure appliance 310 as shown in FIGS. 19A, 19B, wherein a plurality of pin-like acupressure rods 306-1, 306-2 and 306-3 each of which has a non-slip material 304 in the upper end thereof is provided in a base board 303 made of a substrate 300 and a bolster base 302, the height of the rods are increased from the center position to both ends, and legs 308 made of an elastic body are provided under the substrate 300.

When this acupressure appliance 310 is used, the acupressure points 211, 212, 214 and 216 and/or peripheries thereof in the vicinity of the atlas vertebra which is positioned uppermost in the cervical vertebra as shown in FIG. 18C are pressed with each of the acupressure rods 306-1, 306-2 and 306-3.

The following Patent Document 2 also discloses a sound sleep pillow 312 as shown in FIGS. 20A, 20B for removing the symptom of stiff shoulders and eyestrain by stimulating acupressure points in the neck part and on both sides thereof when a user lies on his back, wherein acupressure points on both sides of the neck part are stimulated with convex parts 318 formed on both sides of a semicircular concave part 316 which is formed on the upper surface of a pillow main body 314.

The following Patent Document 3 further discloses an acupressure appliance 319 for neck as shown in FIGS. 21A, 21B to enable pressing acupressure points in the neck (i.e. "fuuchi") in a posture of lying on the back in a configuration that a pillow portion 322 and a pedestal 326 for protruding shafts 324 are formed into a dogleg shape and allowed to turn around a fulcrum 328 with respect to a pedestal 320 of a main body.

The following Patent Document 4 also discloses an acupressure appliance 340 as shown in FIGS. 22A, 22B, 22C, wherein a pair of rectangular columns 332, 332 is erected on the upper surface of a substrate 330 and upper end surfaces of the rectangular columns 332 are molded into smooth projecting curved surfaces 334 on which cover cloths 338 with cotton 336 as a cushion material are arranged.

This acupressure appliance 340 is considered to be effective in improvement of stiff shoulders and stimulation of blood circulation to the head part by bringing the upper ends of the rectangular columns 332 into contact with the base of neck muscles of a user who lies on his back under 342 in usage.

However, none of these appliances disclosed in the above Patent Documents is suitable for pressing muscles in the interscapular regions 202, the upper scapular regions 206 and the rear neck parts 204 as shown in FIG. 18A and the side neck parts 208 as shown in FIG. 18B or other body parts because they are configured mainly for the purpose of pressing acupressure points in the vicinity of the atlas vertebra as shown in FIG. 18C.

PRIOR ART DOCUMENTS

Patent Documents

Patent Document 1: Japanese Patent Application Publication No. 2005-224369

Patent Document 2: Japanese Patent Application Publication No. H11-244113
Patent Document 3: Japanese Patent Application Publication No. 2006-288986
Patent Document 4: Japanese Patent Application Publication No. H5-44130

Non-patent Documents

Non-Patent Document 1: Toru Namikoshi, "Kenkou no izumi shiatsu kyoushitu (fountain of health, acupressure lesson)", 1979, pp. 22, 23, 48 and 72

SUMMARY OF THE INVENTION

Problems to be Solved

The present invention was achieved with the above circumstances as a background and aims at providing an acupressure appliance capable of effectively applying pressure to the interscapular regions and the upper scapular regions or further to the rear neck part and the region in the upper neck from one of the mastoids to the other one or other body parts.

Means for Solving Problems

An acupressure appliance according to a first aspect of the present invention is characterized by comprising: (a) a pair of curved rod-like pressure units each including a solid or hollow structure in an entire or partial manner, each including a convex-curved segment of a chevron shape curved continuously in an axial direction, each formed in a longitudinal shape in the axial direction and formed in a shape having a curved upper side projected upward in transverse cross section, the pair of curved rod-like pressure units spaced apart from each other in a lateral direction perpendicular to the axial direction; and (b) a connector connecting the pair of curved rod-like pressure units in the lateral direction.

An acupressure appliance according to a second aspect of the present invention is characterized by further comprising an adjustment portion configured to adjust an interval between the pair of curved rod-like pressure units in the lateral direction in the first aspect of the present invention.

An acupressure appliance according to a third aspect of the present invention is characterized in that each of the pair of curved rod-like pressure units is made of an elastic body and is curved along a convex-curved upper side of a transverse cross section of the connector so that the convex-curved segment of each of the pair of curved rod-like pressure units is formed, and that the pair of curved rod-like pressure units have a pair of legs protruding from the connector at axial ends of the pair of curved rod-like pressure units, respectively, and the pair of legs are bound to the connector by binding material below the connector so that the pair of curved rod-like pressure units are fixed to the connector, and retained in a curved shape by the connector serving as a shape retainer in the first aspect of the present invention.

An acupressure appliance according to a fourth aspect of the present invention is characterized in that each of the pair of curved rod-like pressure units formed in a straight shape in the axial direction when being molded is forcibly bent along an upper surface of the connector with elastic deformation so that each of the pair of curved rod-like pressure units is deformed into a curved shape having the convex-curved segment corresponding to the upper surface of the connector, and retained in such a curved shape in the third aspect of the present invention.

An acupressure appliance according to a fifth aspect of the present invention is characterized in that at least one of the pair of curved rod-like pressure units is adjustable in a lateral position along the connector in the third aspect or the fourth aspect of the present invention.

An acupressure appliance according to a sixth aspect of the present invention is characterized in that the acupressure appliance is used in such a manner that lower ends of the pair of legs of the pair of curved rod-like pressure units are allowed to abut on an installation surface in the third aspect, the fourth aspect, or the fifth aspect of the present invention.

An acupressure appliance according to a seventh aspect of the present invention is characterized in that each of the pair of curved rod-like pressure units is flattened in the lateral direction at a contact-side surface thereof contacting the connector in the third aspect, the fourth aspect, the fifth aspect, or the sixth aspect of the present invention.

An acupressure appliance according to an eighth aspect of the present invention is characterized in that the connector is formed in a rod shape whose transverse cross section is round in the third aspect, the fourth aspect, the fifth aspect, the sixth aspect, or the seventh aspect of the present invention.

An acupressure appliance according to an ninth aspect of the present invention is characterized in that the connector is made of wood in the eighth aspect of the present invention.

An acupressure appliance according to a tenth aspect of the present invention is characterized in that the binding material is a non-stretchable string in the third aspect, the fourth aspect, the fifth aspect, the sixth aspect, the seventh aspect, the eighth aspect, or the ninth aspect of the present invention.

Advantageous Effects of the Invention

As stated above, according to the present invention, the acupressure appliance is configured by including: a pair of curved rod-like pressure units formed into a longitudinal shape in the axial direction by having convex-curved segments of a chevron shape curved continuously along the axial direction with curved top surfaces projecting upward in the cross section and being spaced apart from each other to be positioned on the right and left sides; and a connector for connecting the pair of pressure units on the right and left sides.

The acupressure appliance can be used as follows for example.

Specifically, the acupressure appliance is placed on an installation surface such as a floor and a user lies on his back on the installation surface such as the floor, then at that time, the pair of pressure units (or peaks and/or peripheries thereof in the convex-curved segments in particular) of the acupressure appliance are fitted to, for example, body parts on the user's back such as the interscapular regions 202, the upper scapular regions 206 and the rear neck parts 204 as shown in FIG. 18A so that the user leans his weight (or partial weight exactly) on the pressure units in this state.

Then, the pressure units press body parts of the user such as the interscapular regions 202, the upper scapular regions 206 and the rear neck parts 204 to loosen muscles and improve blood circulation, whereby providing effects similar to the acupressure therapy.

As an actual method of use, it is preferable to initially fit the pressure units to the interscapular regions 202 of a user who lies on his back and apply pressure to the interscapular regions 202 in this state, subsequently fit the pressure units to the scapular regions 206 and apply pressure thereto after the user moves his body or the acupressure appliance is displaced along an installation surface, and further fit the pressure units to the rear neck parts 204 and apply pressure thereto.

By doing so, it is possible to apply pressure treatment to muscles of respective body parts, which is highly effective in removal or alleviation of the symptom of stiff shoulders.

Although the interval between the right and left sides of the pressure units is slightly different from the interval of the interscapular regions 202, 202, the upper scapular regions 206, 206 or the rear neck parts 204, 204, body parts such as the interscapular regions 202, the upper scapular regions 206 and the rear neck parts 204 or adjacent regions thereof can be pressed while maintaining a fixed interval of the pair of pressure units on the right and left sides by allowing certain latitude on the right and left sides in the curved rod-like pressure units (application of pressure to adjacent regions can also provide certain effects realized by pressure).

The acupressure appliance of the present invention can also press the side neck parts 208 shown in FIG. 18B and/or adjacent regions thereof by expanding the interval of the pair of pressure units to some extent on the right and left sides in a posture assumed by a user who lies on his back.

In the present invention, it is possible to use one of the pair of pressure units and install the pressure unit on an installation surface in a crosswise direction to a user in order to apply pressure to various kinds of acupressure points in the vicinity of the atlas vertebra as shown in FIG. 18C in a position from one side to the other side of the pair of mastoids in the upper neck region by using the pressure unit.

Other than that, the acupressure appliance of the present invention can be used as follows by utilizing its topological features.

Specifically, since each of the pair of pressure units has a curved shape to surround the connector in the acupressure appliance of the present invention, acupressure effects can be generated by using a total of four spots of the pressure units to support the weight at the same time by fitting a portion from the convex-curved segment to one of the legs to the shoulder side, fitting a portion from the convex-curved segment to the other leg to a part from the neck to the head, and a user leaning his weight on the pair of pressure units in this state.

In this case, the weight is supported using the most comfortable spot searched in the area from the interscapular region to the upper scapular region on the shoulder side and the weight is supported using the most comfortable spot searched in the periphery of the mastoid in which pressure effects can be exhibited on the neck or head side.

At this time, more weight should be allotted to the shoulder side and less weight should be allotted to the neck or head side.

Thus, using the acupressure appliance makes it possible to remove or alleviate the symptom of stiff shoulders more effectively.

If only the symptom of stiffness on the shoulder side or only the symptom of stiffness on the neck side is removed, it is not possible to feel that the symptom of stiff shoulders was removed or alleviated sufficiently, but the above method of use allows removal of the symptom of stiffness on both shoulder and neck sides at the same time and can enhance effects of removing or alleviating the symptom of stiff shoulders.

For those who have heavy stiff shoulders, higher pressure effects can be generated by such a method that a user slightly moves his body to lie on his side and leaves his weight to be supported by a total of two spots at the same time including one spot on the shoulder side and one spot on the neck or head side.

When the acupressure appliance is used as stated above, comfortable spots can be easily searched in fitting the pressure units thereto because the top surfaces in the cross section of the pressure units are formed into curved surfaces projecting upward and the pressure units are formed into a convex curved shape as a whole to surround the connector in the acupressure appliance of the present invention.

Explained above are mainly examples of how to use the acupressure appliance for the purpose of removing or alleviating the symptom of stiff shoulders, but the acupressure appliance of the present invention can also be used as an appliance to press various body parts.

In the present invention, the acupressure appliance can also be provided with an adjustment means for adjusting the interval of the pair of pressure units on the right and left sides (according to a second aspect of the present invention).

In this case, the interval of the pair of pressure units on the right and left sides is adjusted appropriately to meet the interval of the interscapular regions 202, 202, the upper scapular regions 206, 206, the rear neck parts 204, 204, or other body parts on the right and left sides, whereby these body parts can be pressed effectively.

In the present invention, the pressure units are composed of an elastic body such as rubber, wherein the pressure units are curved along the convex curved top surface in the cross section of the connector so as to form the convex-curved segments in the periphery of the connector, and the pair of legs protruding from the connector in the axial ends are bound to each other by a binding member under the connector so as to fix the pressure units to the connector while retaining the curved shape of the pressure units by using the connector as a shape retainer (according to a third aspect of the present invention).

The pressure units composed of an elastic body provide good feeling to a user who leans his weight on the pressure units while fitting his respective body parts thereto, and the pressure units can be elastically deformed in the width direction at that time so that particular parts and adjacent parts of the body can be pressed with some latitude and therefore pressure effects can be enhanced.

Although the pressure units can be molded in advance into the finally achieved curved shape in this case, the pressure units provided in the form of a straight shape in the axial direction in the process of molding are forcibly bent along the top surface of the connector with elastic deformation so as to be deformed into a curved shape having the convex-curved segments of a shape corresponding to the top surface while the pressure units are retained in its shape (according to a fourth aspect of the present invention).

According to the fourth aspect of the present invention, the curved shape of the pressure units including the convex-curved segments can be changed variously by changing the curved top surface shape in the cross section of the connector and the pressure units can also be easily brought into an appropriate curved shape by forming the curved top surface shape into a predetermined appropriate shape.

In addition, since the pressure units may be simply molded into a straight shape or the pressure units can be brought into a predetermined curved shape by using an elastic body of a straight shape without making any changes, the acupressure appliance can be configured easily and inexpensively.

In these cases, it is possible to render at least one of the pair of pressure units adjustable in positioning on the right and left sides along the connector (according to a fifth aspect of the present invention).

By doing so, the interval of the pair of pressure units on the right and left sides can be simply adjusted or changed to a desired interval.

The acupressure appliance according to the third aspect, the fourth aspect, or the fifth aspect of the present invention can be used by bringing lower ends of the pair of legs provided in the pressure units into contact with an installation surface (according to a sixth aspect of the present invention).

In this case, it is possible to favorably suppress dislocation of the acupressure appliance in use since the pressure units composed of an elastic body come into close contact with an installation surface and generate a large friction force in a state in which lower ends of the legs are elastically deformed when the acupressure appliance is used by a user who puts his body thereon. Therefore, the acupressure appliance can be used with excellent usability.

The pressure units can be flattened on the right and left sides in contact surfaces to the connector (according to a seventh aspect of the present invention).

By doing so, it is possible to favorably suppress slippage and movement of the pressure units to the right and left sides in the contact parts to the connector in use.

In the present invention, the connector can be formed into a rod shape with a round cross sectional shape. Specifically, the connector can be configured by using a rod member whose cross section has a round shape (according to an eighth aspect of the present invention).

In this case, the connector can be composed of metal, plastic, or other materials but it is preferable to use wood in accordance with a ninth aspect of the present invention (according to a ninth aspect of the present invention).

Meanwhile, a non-stretchable string can be used as the above binding material (according to a tenth aspect of the present invention).

The pressure units can be easily fixed to the connector and the pair of legs in the pressure units can be easily bound to each other by using a non-stretchable string as a binding material.

If a stretchable rubber or another binding material is used as a binding material, the shape of the pressure units are in danger of deviating from an appropriate shape resulting from deformation of the pressure units to a direction to which the pair of legs expand in response to application of a force such as application of user's weight to the pressure units, but such inconvenience can be avoided by using a non-stretchable string.

BRIEF DESCRIPTION OF THE DRAWINGS

For more thorough understanding of the present invention and advantages thereof, the following description should be read in conjunction with the accompanying drawings, in which:

FIG. 13A shows acupressure appliance according to a yet further embodiment of the present invention.

FIG. 13B shows acupressure appliance according to a yet further embodiment of the present invention.

FIG. 15A shows an acupressure appliance according to another embodiment of the present invention.

FIG. 15B shows an acupressure appliance according to another embodiment of the present invention.

FIG. 17A shows usage examples of the acupressure appliances shown in FIGS. 15A, 15B and FIGS. 16A, 16B.

FIG. 17B shows usage examples of the acupressure appliances shown in FIGS. 15A, 15B and FIGS. 16A, 16B.

FIG. 18A is an explanatory diagram showing heretofore known pressure points in acupressure.

FIG. 18B is an explanatory diagram showing heretofore known pressure points in acupressure.

FIG. 18C is an explanatory diagram showing heretofore known pressure points in acupressure.

DESCRIPTION OF EMBODIMENTS OF THE INVENTION

Next, embodiments of the present invention will be explained in detail based on the drawings.

Figure 1:
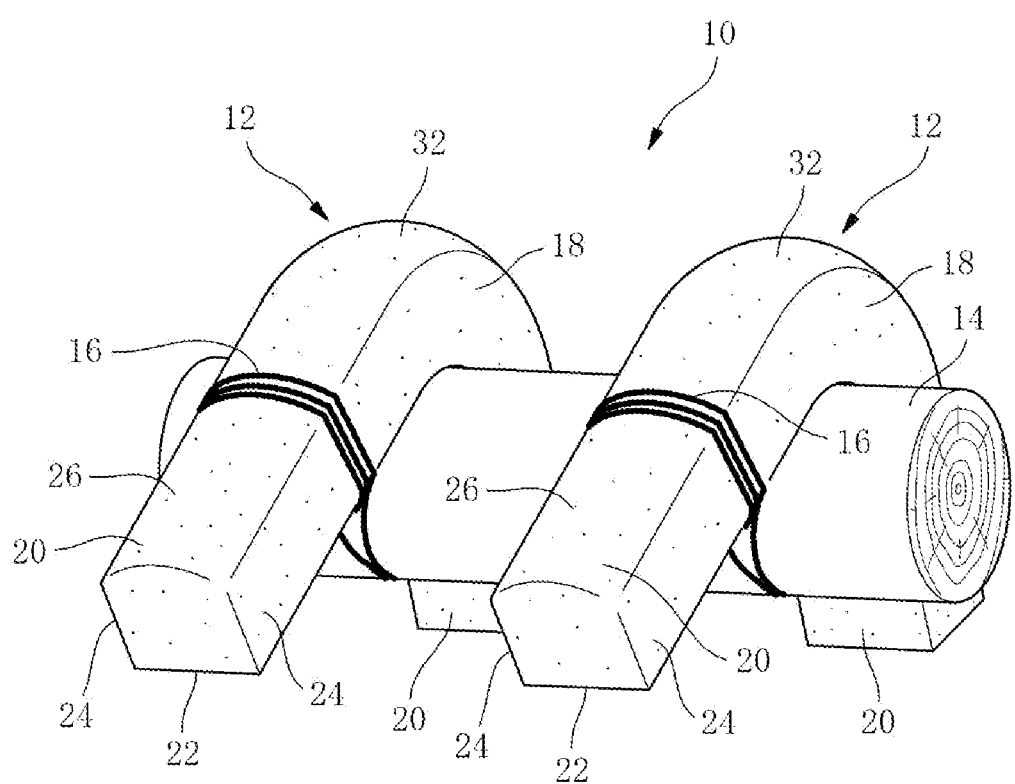
FIG. 1 is a perspective view of an acupressure appliance according to a first embodiment of the present invention.
Figure 2:
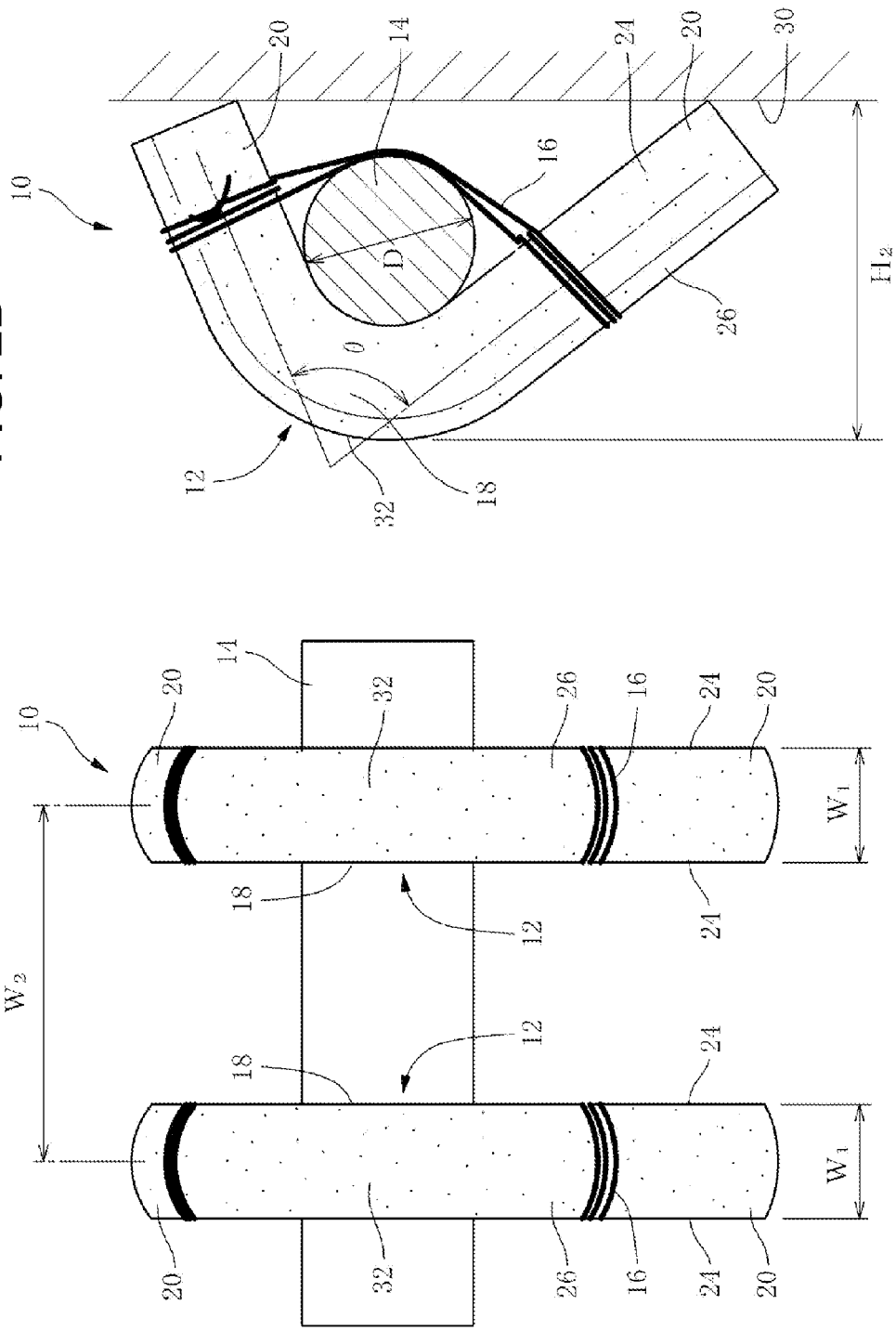
FIG. 2A is a plan view of the acupressure appliance.
FIG. 2B is a side surface view of the acupressure appliance.

In FIG. 1 and FIGS. 2, 10 are an acupressure appliance of the present embodiment, comprising a pair of pressure units 12 and a connector 14 for connecting the pressure units on the right and left sides.

In this embodiment, the connector 14 is composed of wood with a round cross sectional shape.

Here, the cross sectional shape of the connector 14 is circular with a diameter of 60 mm as shown in FIG. 2B.

Meanwhile, the pair of pressure units 12 are made of a rubber elastic body here and formed into a solid curved rod shape in an assembled state.

Figure 3:
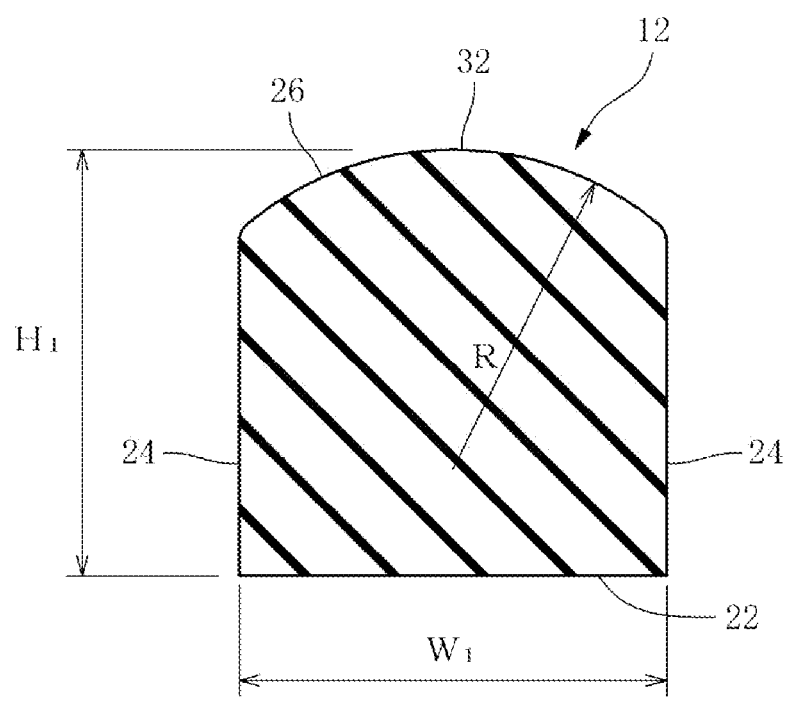
FIG. 3 shows a cross sectional shape of pressure units in the acupressure appliance.

The cross sectional shape thereof is substantially rectangular as shown in FIG. 3, wherein an undersurface 22 serving as a contact surface to the connector 14 and a pair of side surfaces 24 are formed into a flat surface and the pair of side surfaces 24 and the undersurface 22 form right angles with each other.

In contrast, a top surface 26 in FIG. 3 is formed into an arc shape with a radius R.

In this embodiment, dimensions of each parts are set to $W_1$=40 mm, $H_1$=40 mm and R=30 mm.

The pair of pressure units 12 are arranged by being spaced apart from each other on the right and left sides in a direction perpendicular to the axial direction as shown in FIG. 1 and each of them is fixed to the connector 14 by a string 16 serving as a binding material.

Here, the pressure units 12 made of a rubber elastic body is provided in a straight shape in the axial direction in the process of molding.

The pair of pressure units 12 in the form of such a straight shape in the stage of molding are forcibly bent along the top surface of the connector 14 with elastic deformation, whereby convex-curved segments 18 of a shape corresponding to an arc-shaped top surface of the connector 14 are formed, and each of two pairs of legs 20 protruding from the connector 14 is bound to each other by the string 16 serving as a binding material under the connector 14 so as to fix the pair of pressure units 12 to the connector 14 while the pressure units 12 are retained in a predetermined curved shape by using the connector 14 as a shape retainer.

Here, the convex-curved segments 18 are formed into a chevron shape which is continuously curved along the axial direction and top surfaces 26 in the cross section are formed into an arc-like curved surface projecting upward. 32 refers to a peak of each of the convex-curved segments 18.

The undersurface 22 shown in FIG. 3 is also elastically brought into contact with the connector 14.

In the pair of pressure units 12, each of the legs 20 protrudes downward below the connector 14 in an assembled state as shown in FIG. 2B.

When the acupressure appliance 10 is used, it is installed on an installation surface 30 in a state that lower ends of the legs 20 abut on the installation surface 30.

As shown in FIG. 2B, the string 16 is fixed in a state of being wound around each of the legs 20 in a position above the lower end of the connector 14 and the string 16 is pressed onto an undersurface of the connector 14 based on the elastic reaction force to make the pair of pressure units 12 return to the original shape.

The acupressure appliance 10 has a height of $H_2$ in an installed state as shown in FIG. 2B. Although $H_2$ is 135 mm in the present embodiment, it is desirably set in a range of 90 to 140 mm.

The pair of legs 20, 20 also form a predetermined angle θ. θ is desirably an acute angle of 90 degrees or less and θ of 70±10 degrees is particularly preferable in the present embodiment.

Here, the angle θ can be made smaller from the state shown in FIG. 2B by forcibly causing elastic deformation of the pressure units 12 to a direction to which the pair of legs 20 approach each other and binding the pair of legs 20 to each other using the string 16 in this state. On the contrary, the angle θ can be made larger by deforming the pressure units 12 to a direction to which the pair of legs 20 are spaced apart from each other and binding the legs 20 using the string 16 in this state.

Meanwhile, an interval $W_2$ between the right and left sides of the pressure units 12, 12 in the acupressure appliance 10 as shown in FIG. 2A is 110 mm. However, the interval $W_2$ can be changed by moving the position of the pressure units 12 to the right and left sides.

In the acupressure appliance 10, the position of the pair of pressure units 12 can be moved along by sliding the pressure units 12 against a friction force generated with the connector 14 by forcibly applying a force to the pressure units 12 to the right and left sides while they are bound by the string 16.

However, unless a force for movement is applied, the pair of pressure units 12 in use are prevented from moving position based on a strong friction force generated with the connector 14.

In moving the position of the pressure units 12 to the right and left sides, it is possible to adjust the position of the pressure units 12 by elastically deforming the pressure units 12 to a direction to which the pair of legs 20 approach each other, followed by shifting the position of the pressure units 12 in this state to the right and left sides along the connector 14 or by moving the position of the pressure units 12 to the right and left sides after untying the bond by the string 16 in some cases and then binding the pair of legs 20 again in this moved state using the string 16.

FIG. 4A to FIG. 9B show usage examples of the acupressure appliance 10 according to the present embodiment.

Figure 4A:
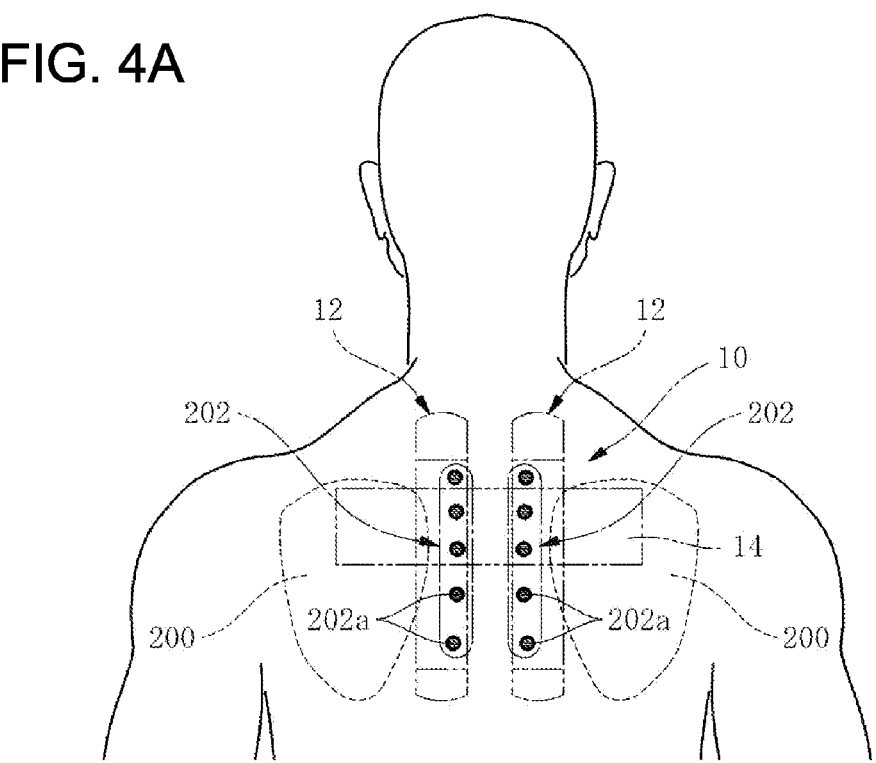
FIG. 4A shows a usage example of the acupressure appliance.
Figure 4B:
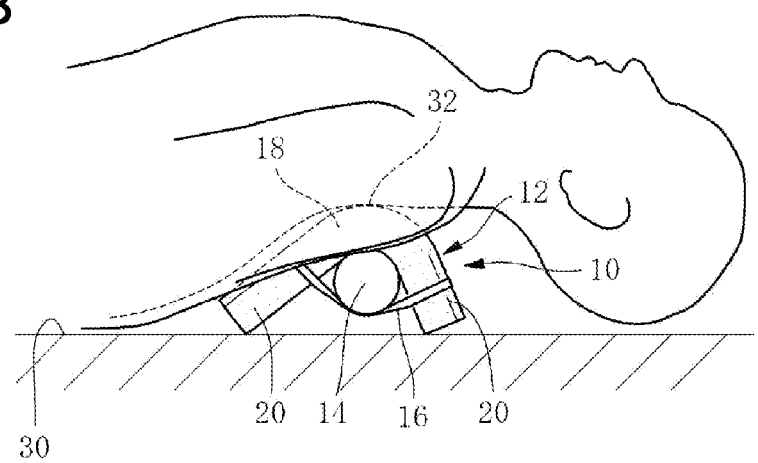
FIG. 4B shows a usage example of the acupressure appliance.

As shown in FIGS. 4A and 4B, the acupressure appliance 10 of the present embodiment is placed on the installation surface 30 such as a floor surface and a user lies on his back on the installation surface 30, wherein the pair of pressure units 12 (or the peaks 32 and/or peripheries thereof in the convex-curved segments 18 in particular) are fitted to the interscapular regions 202 and the user leans his weight (or more specifically partial weight) on the pressure units 12 in this state.

Then, the pressure units 12 or particularly the peaks 32 and/or peripheries thereof in the convex-curved segments 18 press the interscapular regions 202 of the user to loosen muscles and improve blood circulation, whereby providing effects similar to the acupressure treatment.

At this time, because of the predetermined width $W_1$ of each of the pair of pressure units 12 on the right and left sides, not only the pressure points 202a in the interscapular regions 202 but also peripheries thereof on the right and left sides in the drawings can also be pressed corresponding to the width $W_1$.

When the interscapular regions 202 are pressed by the pressure units 12, a user moves his body to shift the position of the interscapular regions 202 to the vertical direction in FIGS. 4A and 4B relative to the convex-curved segments 18 or the position of the convex-curved segments 18 of the acupressure appliance 10 is shifted along the interscapular regions 202, whereby each of the pressure points 202a in the interscapular regions 202 can be pressed sequentially by the convex-curved segments and/or peripheries thereof.

Figure 5:
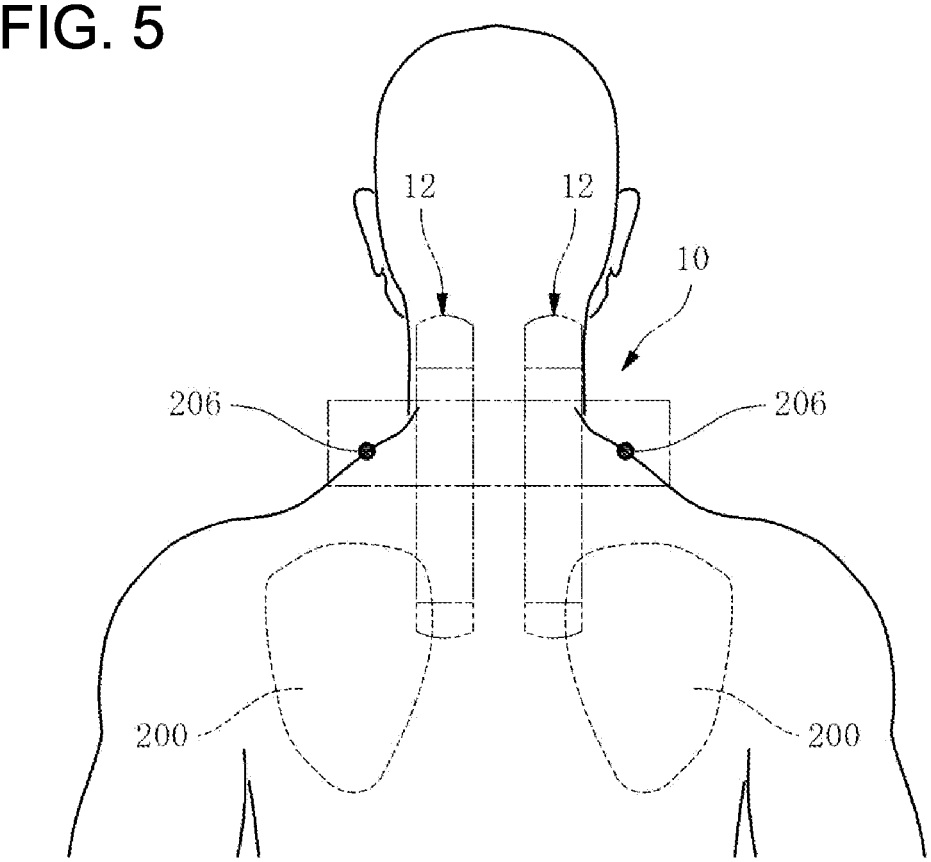
FIG. 5 shows another usage example of the acupressure appliance.

FIG. 5 shows another usage example, wherein the peaks 32 and/or peripheries thereof in the convex-curved segments 18 of the pair of pressure units 12, 12 are fitted to the vicinity of the upper scapular regions 206 and a user who lies on his back partially leans his weight thereon in this state, whereby the vicinity of the upper scapular regions 206 can be pressed by the pressure units 12.

Figure 6A:
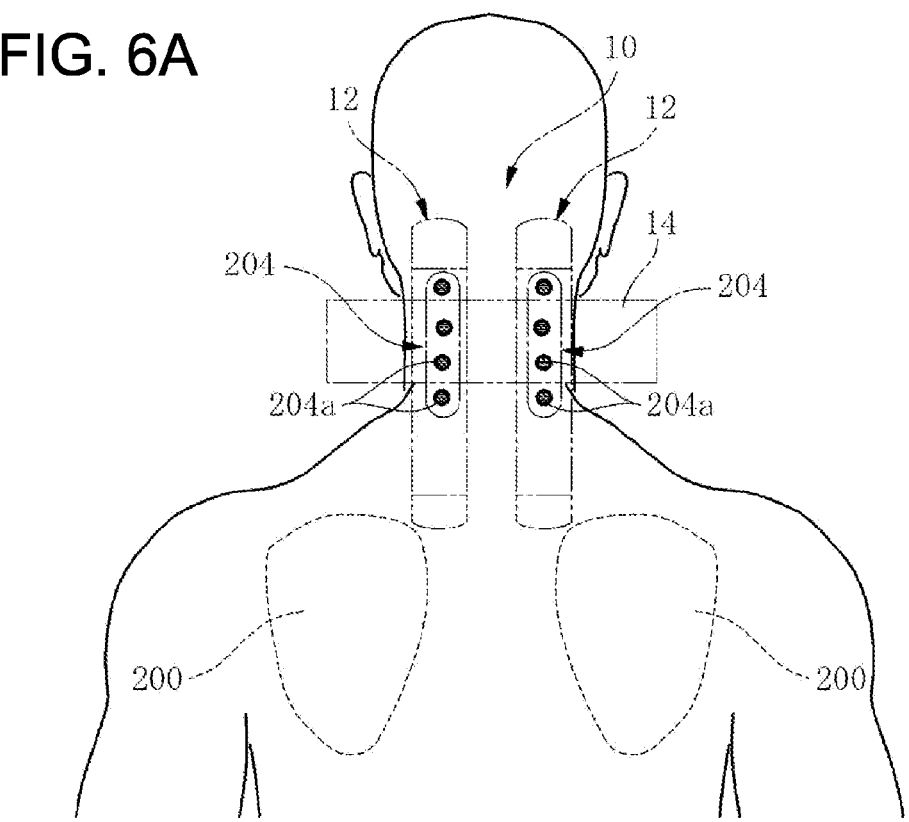
FIG. 6A shows yet another usage example of the acupressure appliance.
Figure 6B:
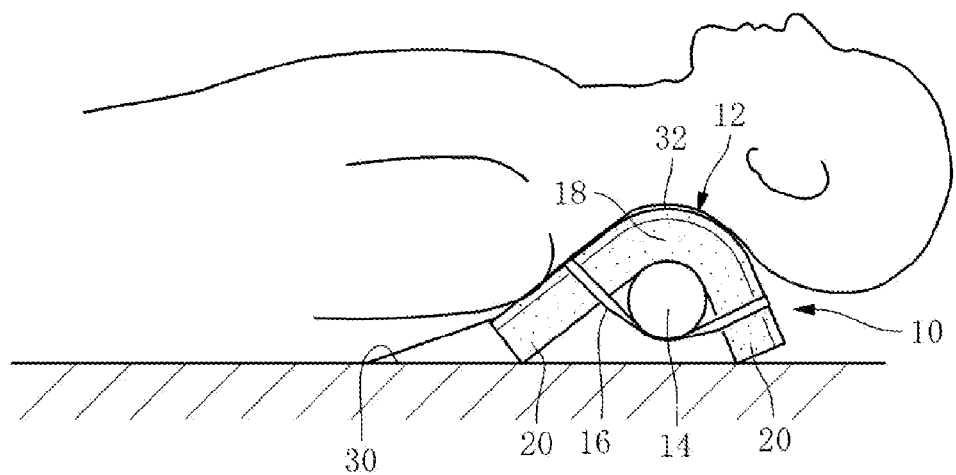
FIG. 6B shows yet another usage example of the acupressure appliance.
Figure 7:
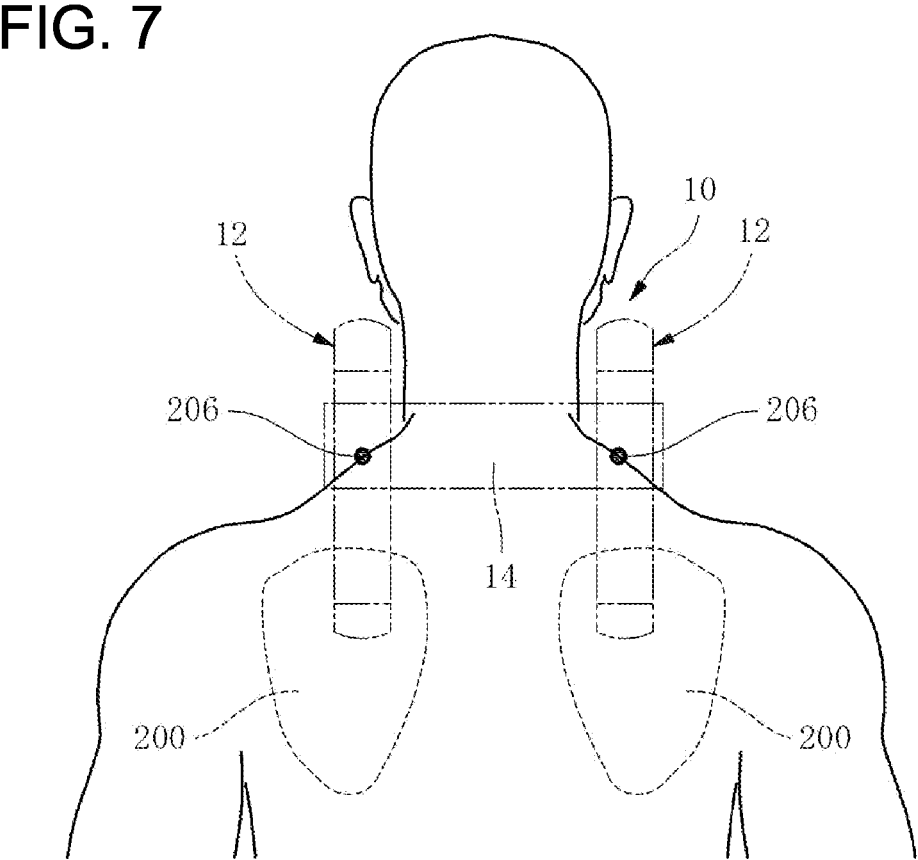
FIG. 7 shows a further usage example of the acupressure appliance.

FIGS. 6A and 6B show yet another usage example.

In this usage example, the pair of pressure units 12 are fitted to the rear neck parts 204 of a user who lies on his back and the user partially leans his weight thereon in this state, whereby the rear neck parts 204 can be pressed by the pressure units 12.

It is also possible in this usage example of FIGS. 6A and 6B to sequentially press each of the pressure points 204a in the rear neck parts 204 by a user moving his body to shift the position of the rear neck parts 204 in the vertical direction in FIGS. 6A and 6B relative to the peaks 32 of the convex-curved segments 18 or by shifting the position of the convex-curved segments 18 of the acupressure appliance 10 sequentially along the rear neck parts 204.

The interval of the pair of pressure units 12 on the right and left sides is fixed in the usage examples of FIG. 4A to FIG. 6B. Therefore, each of the body parts can be pressed in the order of pressing the interscapular regions 202 according to the usage example of FIGS. 4A and 4B, then pressing the vicinity of the upper scapular regions 206 according to the usage example of FIG. 5 by a user shifting his body or shifting the position of the acupressure appliance 10, and further pressing the rear neck parts 204 sequentially according to the usage example of FIGS. 6A and 6B (or in the reverse order).

However, it is of course possible during the above process to make an adjustment to position the interval of the pair of pressure units 12, 12 on the right and left sides to fit a target body part to press as needed.

In the usage example of FIG. 5, the interval of the pair of pressure units 12 on the right and left sides is slightly narrower than the interval of the upper scapular regions 206, 206 and even in such a case, a certain pressure effect can be provided by pressing the vicinity of the upper scapular regions 206 using the pressure units 12. It is also possible as shown in a usage example of FIG. 7 to press the upper scapular regions 206 by the pressure units 12 (or the peaks 32 and/or peripheries thereof in the convex-curved segments 18 in particular) in a state that the interval of the pair of pressure units 12, 12 on the right and left sides is expanded, or specifically, the interval of the pair of pressure units 12, 12 is adjusted to meet the interval of the upper scapular regions 206, 206.

In addition, the side neck parts 208 and/or peripheries thereof can be pressed by the pressure units 12 by adjusting the position of the interval of the pair of pressure units 12, 12 on the right and left sides so as to meet the interval of the side neck parts 208 shown in FIG. 18B (i.e. the interval between the side neck part 208 on the left and the side neck part 208 on the right) and a user lies on his back in this state.

Alternatively, the pressure units 12 can be used such that a user moves his body from the above state to a posture of lying on his side and puts one of the side neck parts 208 on the right and left on one of the pair of pressure units 12 in order to press the side neck part 208 upward by the pressure unit 12.

Figure 9A:
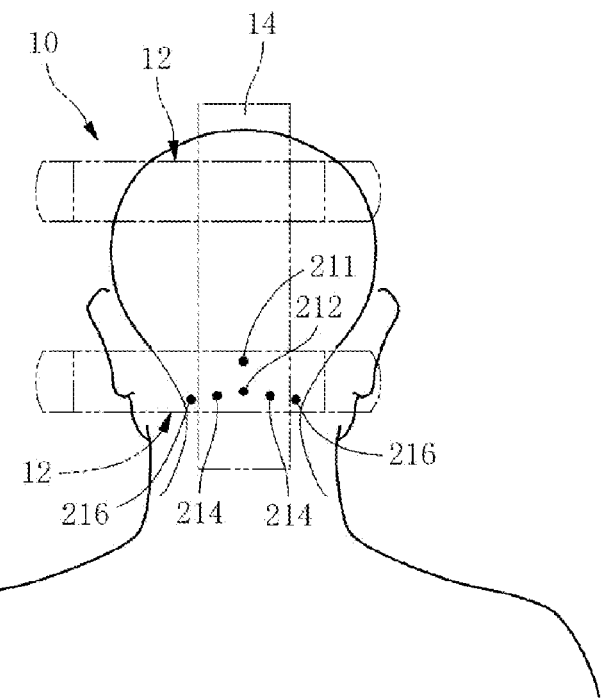
FIG. 9A shows another usage example of the acupressure appliance.
Figure 9B:
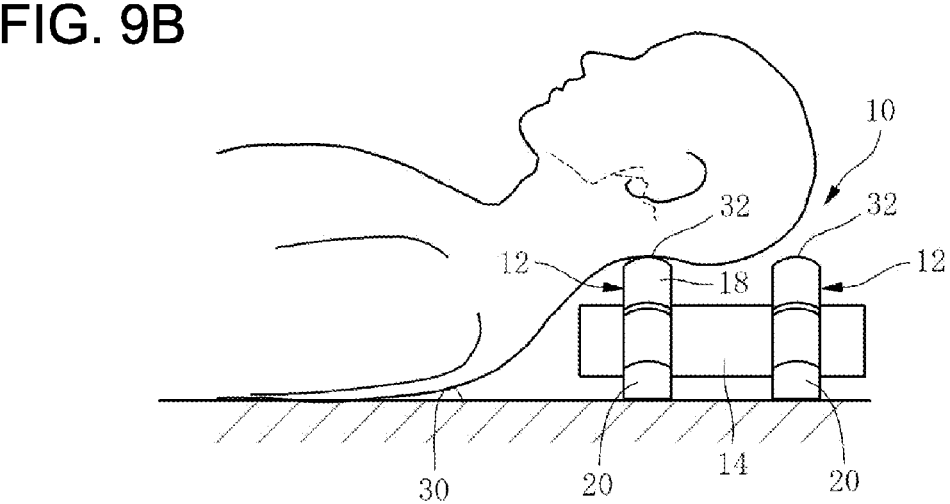
FIG. 9B shows another usage example of the acupressure appliance.

FIGS. 9A and 9B show another usage example of the acupressure appliance 10.

This example is provided for pressing each of acupressure points positioned along the upper neck in a space from one of the pair of mastoids to the other one, or specifically, each of acupressure points such as "fuuchi" 216, "tenchuu" 214, "amon" 212 and "fuuchi" 211 as shown in FIG. 18C, wherein the pressure units 12 used at this time are fitted to press the upper neck in a state that the direction of the acupressure appliance 10 is shifted by 90 degrees from the above usage example in order to position the pressure units 12 along these acupressure points as shown in FIG. 9B.

At this time, a user moves his position by turning his neck to assume a posture of lying on his side from a posture of lying on his back so that each of the acupressure points on the right and left sides is pressed sequentially from "fuuchi" 216 on one side to "fuuchi" 216 on the other side as shown in FIG. 18C, whereby each of the acupressure points can be pressed sequentially by the peaks 32 and/or peripheries thereof in the convex-curved segments 18.

Figure 8A:
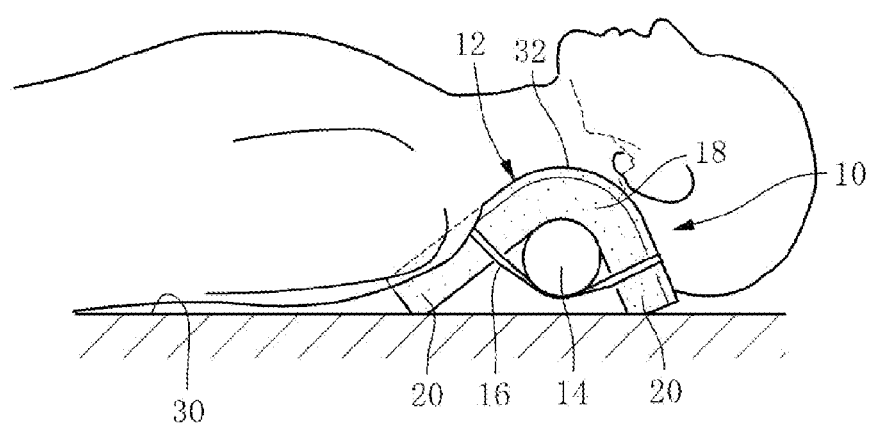
FIG. 8A shows a yet further usage example of the acupressure appliance.

Other than that, the acupressure appliance 10 of the present embodiment can be used as shown in FIG. 8A by utilizing its topological features.

Specifically, owing to the structure of the acupressure appliance 10 provided with the pair of pressure units 12 each of which is formed into a curved shape to surround the connector 14, a user leans his weight on the pair of pressure units 12 in a state that a portion from the convex-curved segment 18 to one of the legs 20 is fitted to the shoulder side and a portion from the convex-curved segment 18 to the other leg 20 is fitted to a part from the neck to the head, whereby the weight is supported by a total of four spots of the pressure units 12 at the same time so as to generate a pressure effect.

In this case, the weight is supported using the most comfortable spot searched in the area from the interscapular region to the upper scapular region on the shoulder side and the weight is supported using the most comfortable spot searched in the vicinity of the mastoid on the neck or head side in which a pressure effect is exhibited.

At this time, more weight should be allotted to the shoulder side and less weight should be allotted to the neck or head side.

Thus using the acupressure appliance 10 enables more effective removal or alleviation of the symptom of stiff shoulders.

If only the symptom of stiffness on the shoulder side or only the symptom of stiffness on the neck side is removed, it is not possible to feel that the symptom of stiff shoulders was removed or alleviated sufficiently, but the above method of use makes it possible to remove the symptom of stiffness on both shoulder and neck sides at the same time, whereby effects of removing or alleviating the symptom of stiff shoulders can be enhanced.

Figure 8B:
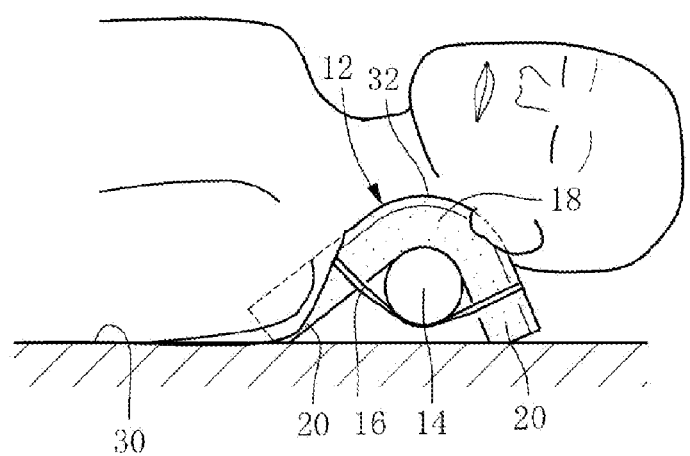
FIG. 8B shows a yet further usage example of the acupressure appliance.

For those who have heavy stiff shoulders, higher pressure effects can be generated by such a method that a user slightly moves his body to lie on his side and leaves his weight to be supported by a total of two spots at the same time including one spot on the shoulder side and one spot on the neck or head side as shown in FIG. 8B.

When the acupressure appliance 10 is used as stated above, owing to the structure of the acupressure appliance 10 in which the top surfaces in the cross section of the pressure units 12 are curved surfaces projecting upward and the pressure units 12 are formed into a convex curved shape as a whole to surround the connector 14, comfortable spots can be easily searched in fitting the pressure units 12 thereon.

Figure 10A:
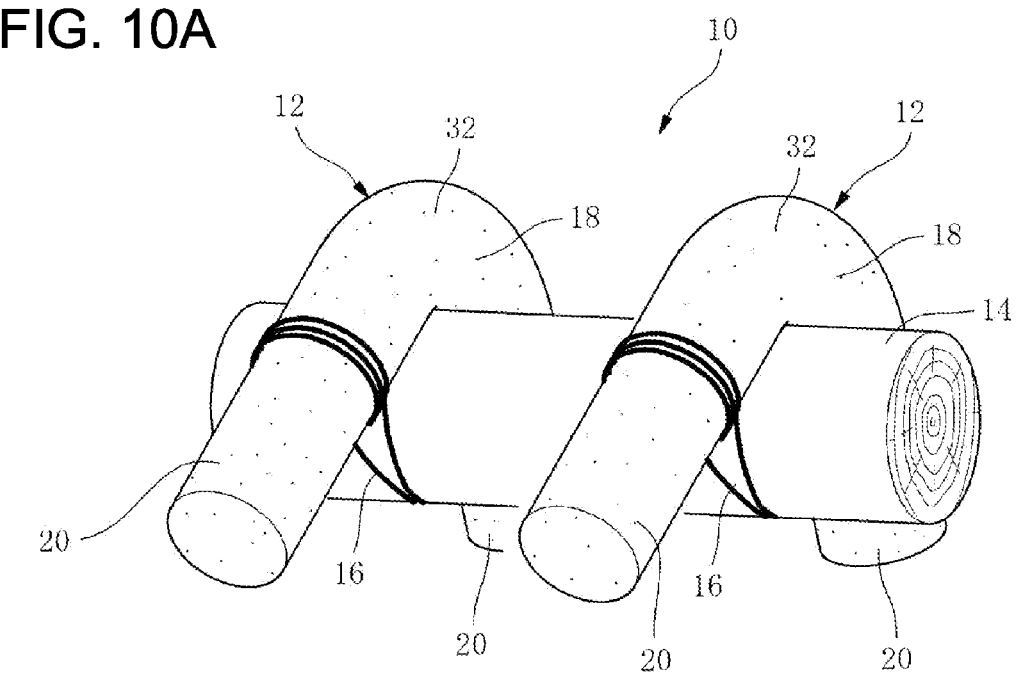
FIG. 10A shows an acupressure appliance according to another embodiment of the present invention.
Figure 10B:
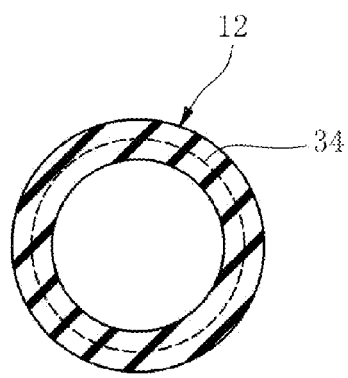
FIG. 10B shows a cross-sectional view of a pressure unit of FIG. 10A.

FIGS. 10A and 10B show another embodiment.

FIG. 10A is an example in which the pressure units 12 are composed of a rubber elastic body with a circular cross section in a solid structure as a whole. Other aspects are basically the same as the acupressure appliance 10 of the above embodiment.

Note that the pressure units 12 can also be configured with a rubber elastic body having a hollow circular cross section (of specifically circular ring shape) as shown in FIG. 10B.

In this case, the pressure units 12 for use preferably have a reinforcing yarn layer 34 provided in an intermediate part in the cross section.

Figure 11:
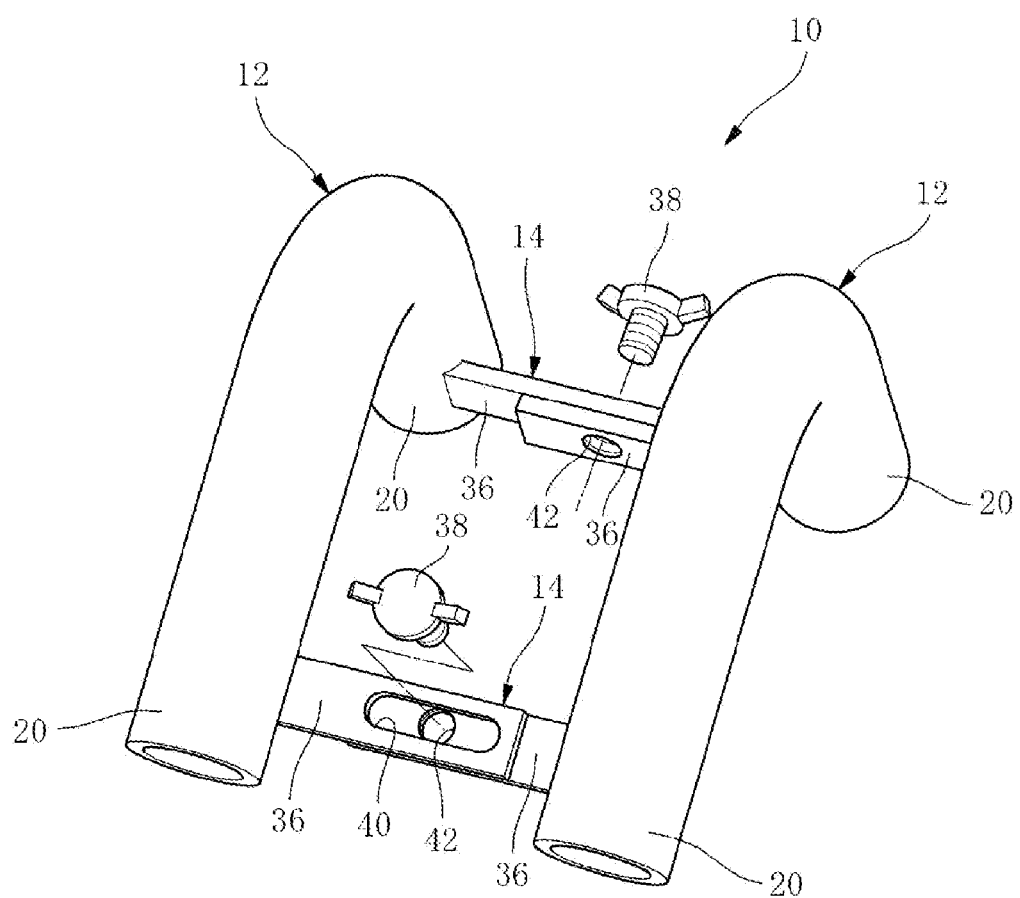
FIG. 11 shows an acupressure appliance according to yet another embodiment of the present invention.

FIG. 11 shows yet another embodiment of the present invention.

In this example, the pressure units 12 are configured by using a hollow pipe made of hard resin of a curved rod shape as a whole.

It is also possible to configure the pressure units 12 with the use of hard materials other than resin.

Outer surfaces of the pressure units 12 can also be coated and formed with an elastic material.

It is further possible to attach an elastic cap such as rubber to lower ends of the pair of legs 20.

In this embodiment, arms 36 are extended from the legs 20 of the respective pressure units 12 and fastened by a locking screw 38 to constitute the connectors 14.

Here, one of the arms 36 is provided with a long hole 40 and the other arm 36 is provided with a circular female screw hole 42 and the long hole 40 is moved to the right or left side in FIG. 11 relative to the locking screw 38, whereby the interval of the pair of pressure units 12, 12 on the right and left sides can be adjusted.

Specifically, the long hole 40, the female screw hole 42 and the locking screw 38 here constitute a positional adjustment means.

Figure 12A:
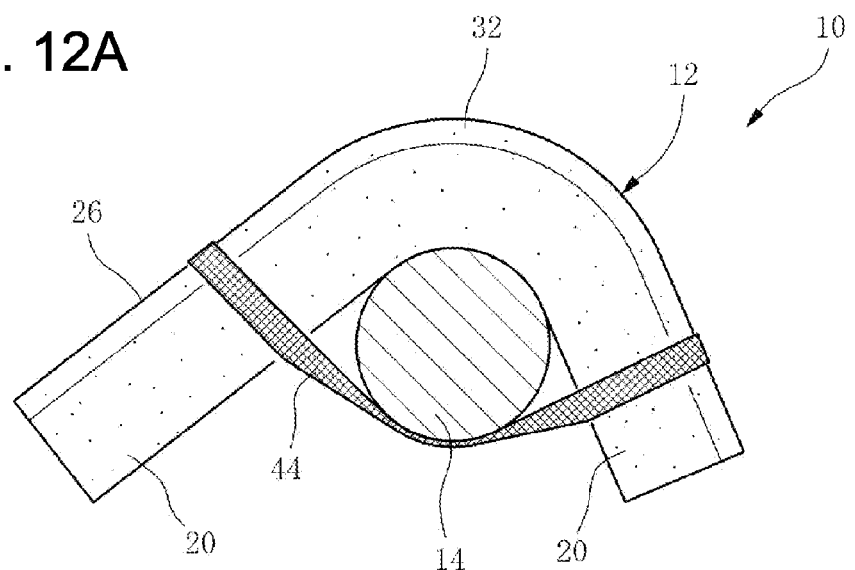
FIG. 12A shows an acupressure appliance according to a further embodiment of the present invention.
Figure 12B:
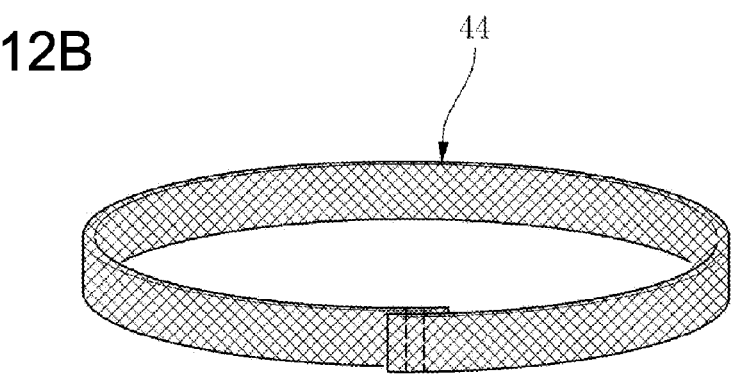
FIG. 12B shows a perspective view of annular band of FIG. 12A.

FIGS. 12A and 12B show a further embodiment of the present invention.

In this example, in place of the string 16, a flexible (or non-stretchable if possible) annular band 44 of a predetermined circumference prepared by sewing both ends in advance as shown in FIG. 12B is used to bind the pair of pressure units 12 and fix them to the connector 14.

In this example, the pressure units 12 can be fixed to the connector 14 while retaining a predetermined curved shape as shown in FIG. 12A by fitting the annular band 44 to the outer periphery of the pair of legs 20 from both ends of the pressure units 12 that are forcibly bent along the top surface of the connector 14 with elastic deformation, whereby making it easy work to fix the pressure units.

FIGS. 13A, 13B and FIGS. 14A, 14B, 14C show a yet further embodiment of the present invention.

In this example, the connector 14 is composed of round rod-like wood with a circular cross section and the pair of pressure units 12 are composed of a rubber elastic body, which is the same as the first embodiment as shown in FIG. 1 to FIG. 3.

However, the pressure units 12 here use a rubber elastic body having a semicircular cross sectional shape and each of the pressure units 12 is provided with a hollow part 50 having a similar semicircular cross sectional shape through a predetermined length in the axial direction.

Figure 14A:
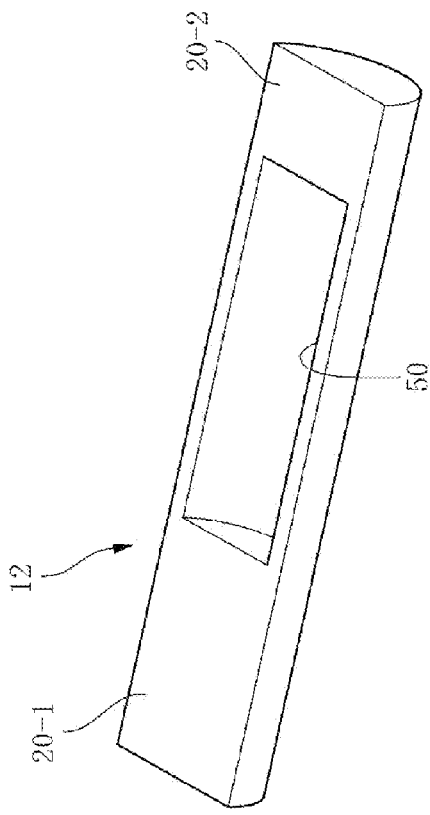
FIG. 14A shows a perspective view of a pressure unit of FIGS. 13A, 13B.
Figure 14B:
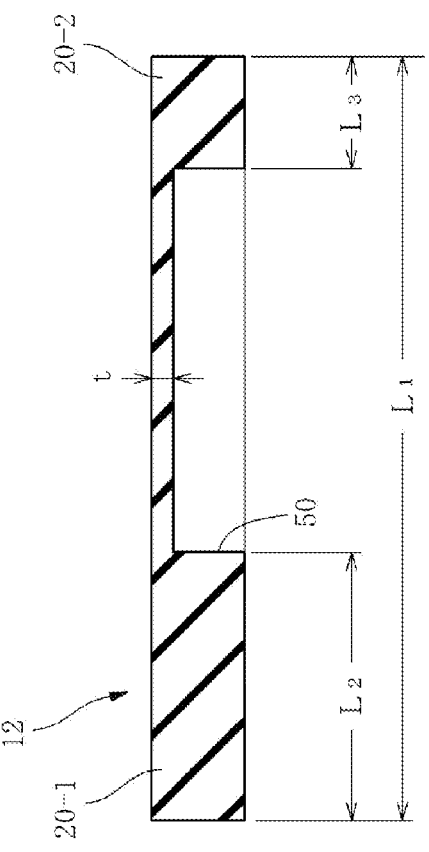
FIG. 14B shows a cross-sectional view of a pressure unit in a longitudinal direction of FIGS. 13A, 13B.
Figure 14C:
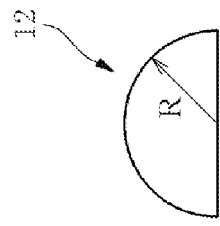
FIG. 14C shows a side view of a pressure unit of FIGS. 13A, 13B.

Here, the pressure units 12 are provided in a straight shape in the axial direction in the process of molding as shown in FIGS. 14A, 14B, 14C and formed into a predetermined curved shape by being assembled onto the connector 14 as shown in FIGS. 13A and 13B.

The shape of the hollow parts 50 in the pressure units 12 in the process of molding is set to 160 mm in an equation of "$L_1-(L_2+L_3)$" in which $L_2$ (=60 mm) and $L_3$ (=30 mm) as lengths of solid portions in both ends of the pressure unit 12 are deducted from $L_1$ (=250 mm) which is an entire length thereof, and a thickness t of the pressure unit 12 in a portion in which the hollow part 50 is arranged falls in a range of 5 to 7 mm.

Note that the semicircular cross section of the pressure unit 12 is of a size whose radius R is 25 mm and the connector 14 has a diameter D of 64 mm.

In the assembled state of FIGS. 13A and 13B, the pressure units 12 are formed into a wide shape due to elastic deformation of a rubber elastic body into a flat shape in positions of the hollow part 50 or in particular in the peaks 32 and peripheries thereof.

Here, a width $W_3$ of each of the peaks 32 is 70 mm as opposed to a width dimension $W_1$ of 50 mm in each of legs 20-1 and 20-2.

Note that other configurations excluding the dimensional relationship are basically the same as the first embodiment shown in FIG. 1 to FIG. 3.

It is also possible to preferably use the acupressure appliance 10 of this example as an appliance for removing or alleviating the symptom of stiff shoulders in the same manner as the acupressure appliances 10 shown in FIG. 1 to FIG. 9B.

Particularly, when the acupressure appliance 10 of this embodiment is used as shown in FIG. 8A by fitting a portion of the leg 20-1 in the solid structure with the length $L_2$ to the shoulder side and fitting a portion of the hollow part 50 to the neck part, it is possible to press the shoulder part by a hard portion of the leg part 20-1 and softly press the neck part by a portion in which the hollow part 50 is positioned.

At this time, owing to the structure of this embodiment in which the peaks 32 and peripheries thereof have a wide shape by arrangement of the hollow parts 50, the neck part can be pressed in a wide range around the neck.

It is further possible to support the weight of a user firmly by the solid portions of the legs 20-1 and 20-2 in the axial ends.

FIGS. 15A and 15B show another embodiment of the present invention.

The connector 14 in this example is also composed of round rod-like wood with a circular cross section, onto which the pair of pressure units 12 made of a rubber elastic body are also assembled to constitute the acupressure appliance 10 as a whole in the same manner as the embodiment shown in FIG. 1 to FIG. 3.

In this example, the pressure units 12 are provided in a straight shape in the axial direction in the process of molding and have a semicircular cross sectional shape in the same manner as the embodiment shown in FIGS. 13A, 13B and FIGS. 14A, 14B, 14C.

However, in the embodiment shown in FIGS. 15A and 15B, the pressure units 12 have a solid structure as a whole without having a partial hollow structure.

In this embodiment, the pressure units 12 have a large semicircular cross sectional shape with the radius R of 40 mm and the width $W_1$ of 80 mm which is wide.

The connector 14 is also formed with the diameter D of 40 mm in the thickness and the pressure units 12 are further set to have a wide angle with a curved angle θ of about 150 degrees.

Note that other embodiments excluding the dimensional relationship are basically the same as the embodiment shown in FIG. 1 to FIG. 3.

Although the acupressure appliance 10 of this example can also be used for stiff shoulders, it can be preferably used for particular purposes such as solving stiffness of back muscles and strengthening back muscles by fitting the pressure units 12 to back muscles of a user as shown in FIG. 17A and pressing back muscles with the use of user's weight.

Although the acupressure appliance 10 in use is fitted upward to back muscles of a user who lies on his back in FIG. 17A, a user can assume a posture of lying on his side to fit one of the two pressure units 12 to back muscles transversely and fitting the other pressure unit 12 to the abdominal part, whereby the pressure units 12 can be used to press not only the side of back muscles but also abdominal muscles.

It is further possible to use the acupressure appliance 10 for pressing the lower abdominal part upward by fitting the pair of pressure units 12 to the lower abdominal part of a user who assumes a posture of lying on his stomach. Thus, effects of removing the symptom of constipation can be achieved by slowly stirring the large intestine and the rectum.

Figure 16A:
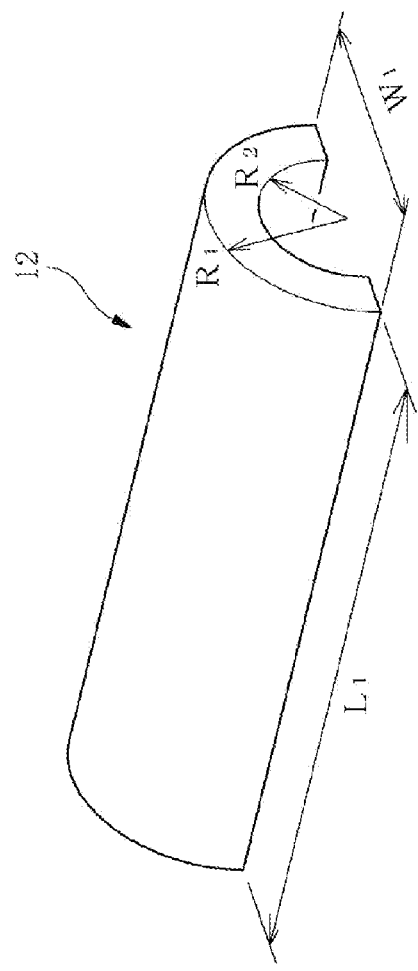
FIG. 16A shows an acupressure appliance according to yet another embodiment of the present invention.
Figure 16B:
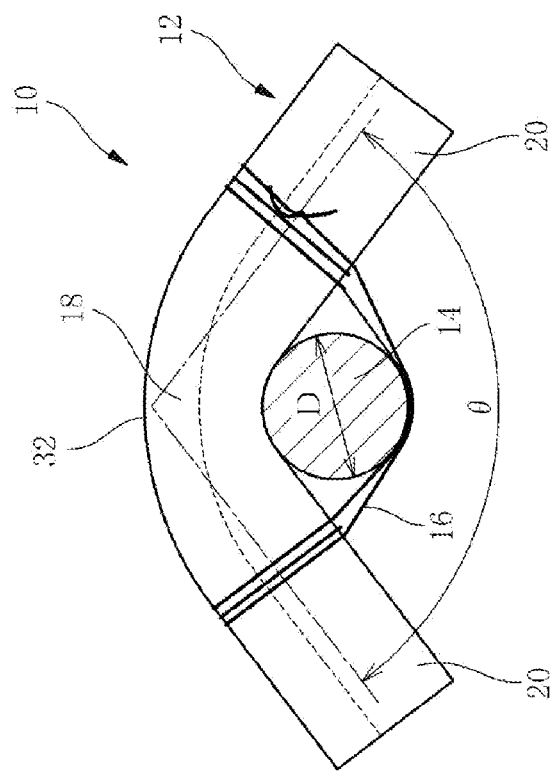
FIG. 16B shows an acupressure appliance according to yet another embodiment of the present invention.
Figure 19A:
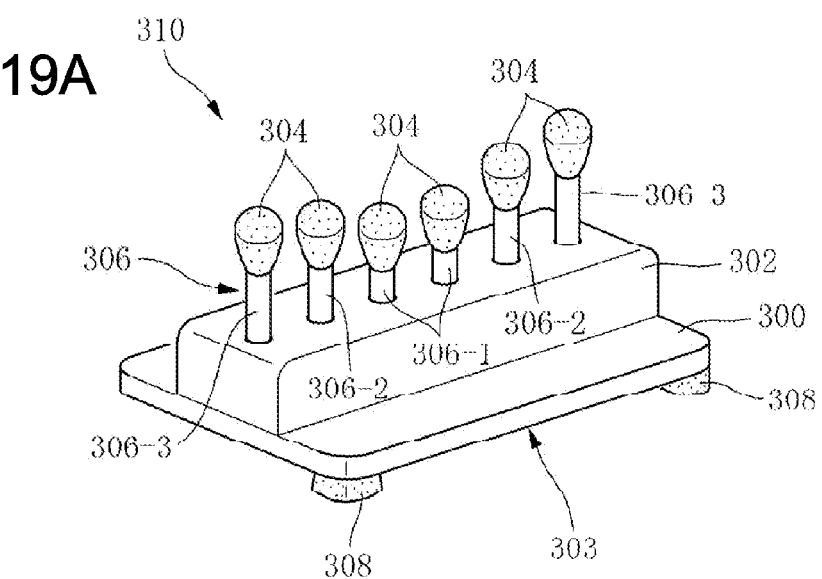
FIG. 19A shows an example of a heretofore known acupressure appliance.
Figure 19B:
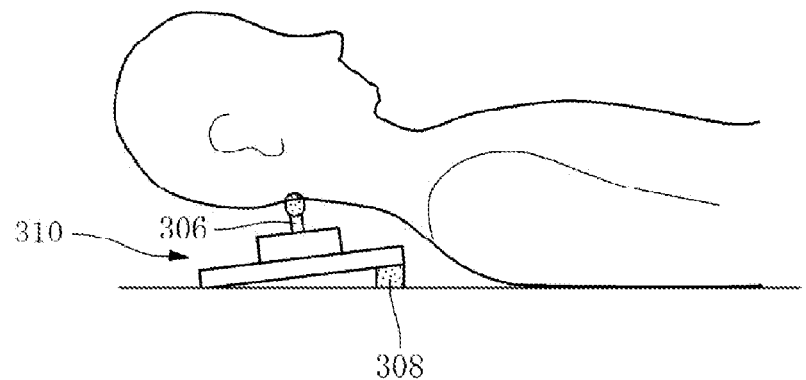
FIG. 19B shows an example of a heretofore known acupressure appliance.
Figure 20:
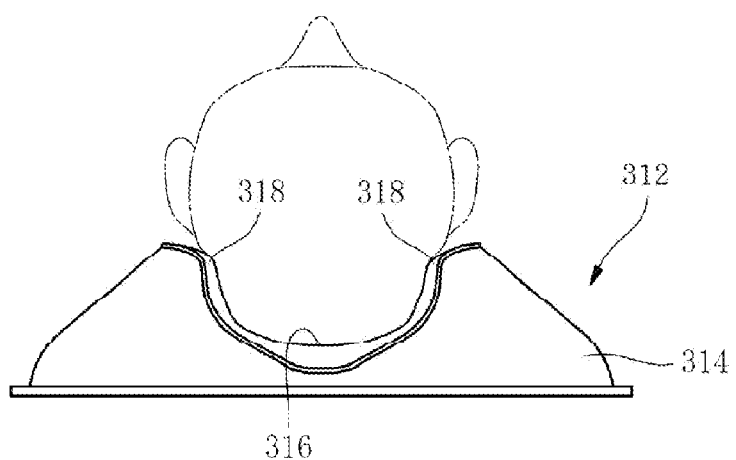
FIG. 20 shows another example of a heretofore known acupressure appliance.
Figure 21A:
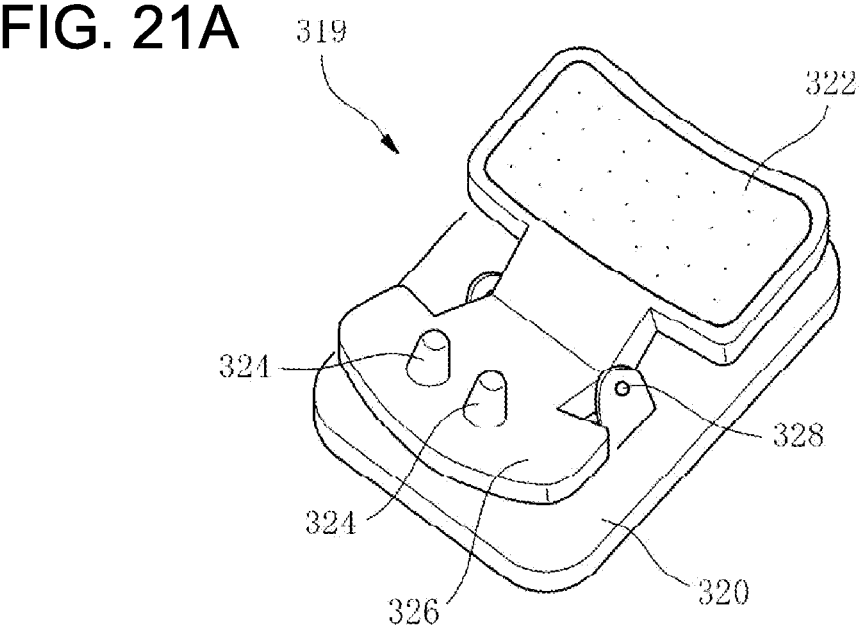
FIG. 21A shows yet another example of a heretofore known acupressure appliance.
Figure 21B:
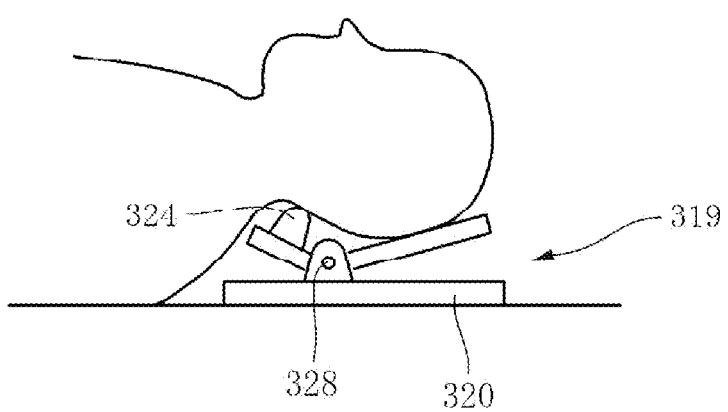
FIG. 21B shows yet another example of a heretofore known acupressure appliance.
Figure 22A:
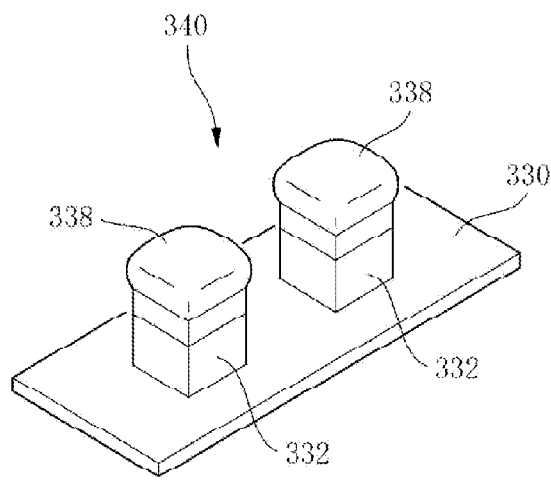
FIG. 22A shows a further example of a heretofore known acupressure appliance.
Figure 22B:
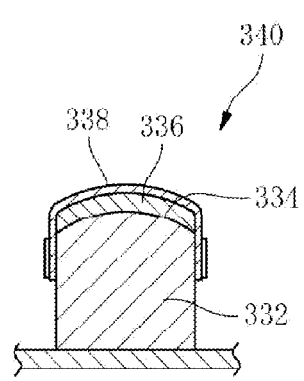
FIG. 22B shows a further example of a heretofore known acupressure appliance.
Figure 22C:
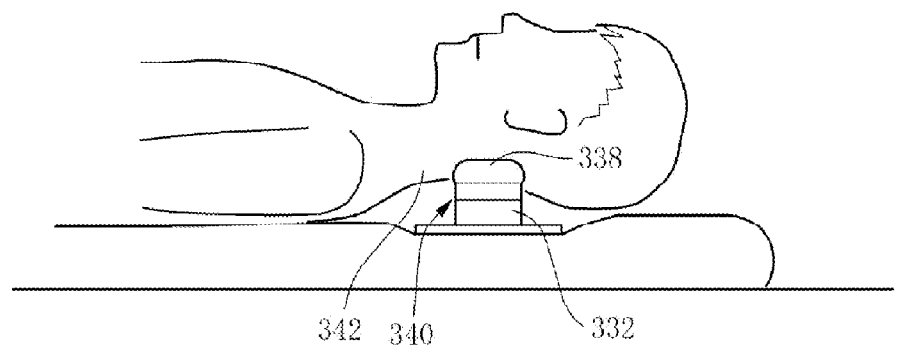
FIG. 22C shows a further example of a heretofore known acupressure appliance.

FIGS. 16A and 16B show yet another embodiment of the present invention.

The connector 14 in this embodiment is also composed of round rod-like wood with a circular cross sectional shape and the pair of pressure units 12 are also made of a rubber elastic body in the same manner as the embodiment shown in FIG. 1 to FIG. 3.

In the embodiment shown in FIGS. 16A and 16B, the pressure unit 12 is formed into a semicircular cross sectional shape, which is the same as the embodiment shown in FIG. 13A to FIG. 14C and the embodiment shown in FIGS. 15A and 15B, but the pressure unit 12 here has a hollow structure through the entire length.

More specifically, the pressure unit 12 in a free form in the process of molding has a semicircular cross sectional shape with a radius $R_1$ of 40 mm in the outer periphery shape and a radius $R_2$ of 25 mm in the inner periphery shape.

Note that the pressure unit 12 has a curved angle θ of 90 to 120 degrees in an assembled shape shown in FIG. 16B with an entire length $L_1$ of 200 mm and a cross sectional width $W_1$ of 80 mm.

Note that other configurations excluding the dimensional relationship are basically the same as the embodiment shown in FIG. 1 to FIG. 3.

Although the acupressure appliance 10 of this example can also be used for stiff shoulders, it is possible to preferably use the acupressure appliance 10 of this example for pressing gluteal muscles in particular.

More specifically, the convex-curved segments 18 of the acupressure appliance 10 are fitted to gluteal muscles of a user who lies on his back as shown in FIG. 17B and the user partially leans his weight on the acupressure appliance 10, whereby making it possible to press gluteal muscles upward from a lower side for strengthening or loosening gluteal muscles by the acupressure appliance 10.

Another preferable way of use is to use both the acupressure appliance 10 shown in FIGS. 15A, 15B and the acupressure appliance 10 shown in FIGS. 16A and 16B in combination, wherein back muscles of a user is pressed as shown in FIG. 17A by using the acupressure appliance 10 of FIGS. 15A, 15B and simultaneously, gluteal muscles of the user is pressed as shown in FIG. 17B by using the acupressure appliance 10 of FIGS. 16A and 16B.

The above acupressure appliances are merely examples and the acupressure appliance of the present invention can also be configured in another embodiment.

The acupressure appliance 10 can also be used in various ways other than the above examples in order to press various body parts.

REFERENCE NUMERALS

10 Acupressure appliance
12 Pressure unit
14 Connector
16 String (binding material)
18 Convex-curved segment
20 Leg
26 Top surface

What is claimed is:

1. An acupressure appliance comprising:
   (a) a pair of curved rod-like pressure units for supporting a body part on an installation surface, each pressure unit including a solid or hollow structure in an entire or partial manner, each including a convex-curved segment of a chevron shape curved continuously in an axial direction, each formed in a longitudinal shape in the axial direction and formed in a shape having a curved upper side projected upward in transverse cross section, the pair of curved rod-like pressure units spaced apart from each other in a lateral direction perpendicular to the axial direction; and
   (b) a connector connecting the pair of curved rod-like pressure units in the lateral direction;
   wherein at least one of the pair of curved rod-like pressure units is positioned along the connector at a location corresponding approximately to an effective pressure point on the supported body part.

2. The acupressure appliance according to claim 1 further comprising an adjustment portion configured to adjust an interval between the pair of curved rod-like pressure units in the lateral direction.

3. The acupressure appliance according to claim 1, wherein each of the pair of curved rod-like pressure units is made of an elastic body and is curved along a convex-curved upper side of a transverse cross section of the connector so that the convex-curved segment of each of the pair of curved rod-like pressure units is formed, and wherein the pair of curved rod-like pressure units have a pair of legs protruding from the connector at axial ends of the pair of curved rod-like pressure units, respectively, and the pair of legs are bound to the connector by binding material below the connector so that the pair of curved rod-like pressure units are fixed to the connector, and retained in a curved shape by the connector serving as a shape retainer.

4. The acupressure appliance according to claim 3, wherein each of the pair of curved rod-like pressure units includes a curved shape with elastic deformation corresponding to the upper surface of the connector.

5. The acupressure appliance according to claim 4, wherein at least one of the pair of curved rod-like pressure units is adjustable in a lateral position along the connector.

6. The acupressure appliance according to claim 4, wherein lower ends of the pair of legs of the pair of curved rod-like pressure units abut the installation surface.

7. The acupressure appliance according to claim 4, wherein each of the pair of curved rod-like pressure units is flattened in the lateral direction at a contact-side surface thereof contacting the connector.

8. The acupressure appliance according to claim 4, wherein the connector is formed in a rod shape whose transverse cross section is round.

9. The acupressure appliance according to claim 8, wherein the connector is made of wood.

10. The acupressure appliance according to claim 4, wherein the binding material is a non-stretchable string.

11. The acupressure appliance according to claim 3, wherein at least one of the pair of curved rod-like pressure units is adjustable in a lateral position along the connector.

12. The acupressure appliance according to claim 3, wherein lower ends of the pair of legs of the pair of curved rod-like pressure units abut the installation surface.

13. The acupressure appliance according to claim 3, wherein each of the pair of curved rod-like pressure units is flattened in the lateral direction at a contact-side surface thereof contacting the connector.

14. The acupressure appliance according to claim 3, wherein the connector is formed in a rod shape whose transverse cross section is round.

15. The acupressure appliance according to claim 14, wherein the connector is made of wood.

16. The acupressure appliance according to claim 3, wherein the binding material is a non-stretchable string.

\* \* \* \* \*